(12) United States Patent
Gudkov et al.

(10) Patent No.: US 9,387,213 B2
(45) Date of Patent: Jul. 12, 2016

(54) SMALL MOLECULES INHIBITING ONCOPROTEIN MYC

(71) Applicants: Health Research, Inc., Buffalo, NY (US); Panacela Labs, Inc., Buffalo, NY (US); Children's Cancer Institute Australia for Medical Research, Randwick (AU)

(72) Inventors: Andrei Gudkov, East Aurora, NY (US); Mikhail Nikiforov, Buffalo, NY (US); Catherine Burkhart, Collins, NY (US); Michelle Haber, Coogee (AU); Murray Norris, Surry Hills (AU)

(73) Assignees: Health Research, Inc., Buffalo, NY (US); Panacela Labs, Inc., Buffalo, NY (US); Children's Cancer Institute Australia for Medical Research, Randwick (AU)

( * ) Notice: Subject to any disclaimer, the term of this patent is extended or adjusted under 35 U.S.C. 154(b) by 0 days.

(21) Appl. No.: 14/434,803

(22) PCT Filed: Oct. 14, 2013

(86) PCT No.: PCT/US2013/064883
§ 371 (c)(1),
(2) Date: Apr. 10, 2015

(87) PCT Pub. No.: WO2014/059429
PCT Pub. Date: Apr. 17, 2014

(65) Prior Publication Data
US 2015/0272960 A1    Oct. 1, 2015

Related U.S. Application Data

(60) Provisional application No. 61/712,933, filed on Oct. 12, 2012.

(51) Int. Cl.
*A61K 31/55* (2006.01)
*A61K 31/44* (2006.01)
*A61K 31/41* (2006.01)
*A61K 31/415* (2006.01)
*A61K 31/416* (2006.01)
*A61K 31/4245* (2006.01)
*A61K 31/473* (2006.01)

(52) U.S. Cl.
CPC .............. *A61K 31/55* (2013.01); *A61K 31/41* (2013.01); *A61K 31/415* (2013.01); *A61K 31/416* (2013.01); *A61K 31/4245* (2013.01); *A61K 31/44* (2013.01); *A61K 31/473* (2013.01)

(58) Field of Classification Search
CPC .............................. C07D 231/12; A61K 31/88
See application file for complete search history.

(56) References Cited

U.S. PATENT DOCUMENTS

2006/0258729 A1* 11/2006 Butler .................... A01N 43/56
514/406

OTHER PUBLICATIONS

Hengst, Bioorganic & Medicinal Chemistry Letters, 2010, vol. 20, p. 7498-7502.*
Fan, C., et al., A novel copper complex of salicylaldehyde pyrazole hydrazone induces apoptisis through up-regulating integrin β4 in H322 lung carcinoma cells, European Journal of Medicinal Chemistry, Apr. 2010, vol. 45, issue 4, pp. 1438-1446.
Chaston, T.B., et al., Examination of the Antiproliferatie Activity of Iron Chelators: Multiple Cellular Targets and the Different Mechanism of Action of Triapine Compared with Desferrioxamine and the Potent Pyridoxal Isonicotyinoyl Hydrazone Analogue 311, Clinical Cancer Research, Jan. 2003, vol. 9, pp. 402-414.
AC1LZ33L-PubChem, CID 1940349, (available at http://pubchem.ncbi.nlm.nih.gov/summary/summary.cgi?cid=1940349&loc=ec__rcs, accessed on Jan. 16, 2014), create date Jul. 13, 2005, 3 pages.

* cited by examiner

*Primary Examiner* — Michael Barker
*Assistant Examiner* — Karen Cheng
(74) *Attorney, Agent, or Firm* — Hodgson Russ LLP

(57) ABSTRACT

Pharmaceutical compositions including a Myc inhibitor are provided. Also provided are methods for treating cancer including administration of compounds that inhibit oncoprotein Myc.

10 Claims, 16 Drawing Sheets

SMALL MOLECULES INHIBITING ONCOPROTEIN MYC

CROSS REFERENCE TO RELATED APPLICATIONS

This application claims priority to U.S. Provisional application No. 61/712,933, filed on Oct. 12, 2012, the disclosure of which is incorporated by reference.

FIELD OF THE DISCLOSURE

The disclosure relates to a method of treating cancer by administering to an individual in thereof a therapeutically effective amount a compound capable of inhibiting the MYC oncoprotein.

BACKGROUND

The Myc family of transcriptional regulators consists of highly conserved, basic helix loop helix (bHLH) containing proteins that regulate cell proliferation, differentiation and apoptosis presumably by activation or repression of the transcription of different sets of target genes. The Myc proteins contain three major domains: 1) the N-terminal domain, which consists of the transactivation and repression domains as well as the two highly conserved (90%) myc box regions (myc box I and myc box II) that are vital for all Myc functions; 2) the central region; and 3) the C-terminal domain that contains the bHLH/leucine rich region required for both DNA binding and dimerization with the bHLH protein Max. Once dimerized with Max, the Myc proteins can bind to the E-box sequence, CACGTG, present in the promoters of target genes and activate transcription. Alternatively, Myc can repress transcription by binding to initiator elements (consensus YYCAYYYYY; Y=pyrimidine) or GC rich regions (e.g., gadd45) in target genes. In addition to Max, Myc proteins interact with a variety of other proteins that facilitate or inhibit various cellular functions, including TRRAP (transactivation through chromatin remodeling, and TFII-1, SP-1 or Miz-1 (repression). Conversely, c-Myc functions are inhibited by interactions with Rb-related p107, Bin1, BRCA1 and p19ARF. Together, these various interactions enable Myc proteins to perform their designated functions in a precise and controlled manner. However, deregulated expression of Myc family members, such as that which results from gene amplification or translocation are found in many cancers.

Recent advances in small molecule drug design and synthesis have resulted in extensive research into molecular-targeted therapy for cancer and the isolation of various small molecules that regulate particular cell functions (e.g., cell cycle, apoptosis, angiogenesis). Such an approach has the potential to be more effective and less toxic than current treatment regimens. Myc function in cells is mediated by a series of interactions between Myc family members and other cellular proteins. Thus, small molecules that are able to interfere with one or more of these interactions have the potential to be developed into anti-Myc drugs. While much of the information on protein-protein interactions has been obtained through functional studies with c-Myc, N-myc is able to substitute for c-Myc under various conditions and should, therefore, be expected to share many of the same interactions. Thus, molecules that are identified in a small molecule screen for one Myc family member would be expected to identify compounds that are active against the other family members. Since Myc proteins function as transcriptional regulators, the use of a reporter (e.g., luciferase) specific for Myc-mediated transcription can be used to detect alterations in Myc activity within cells in the presence of novel small molecules.

N-myc gene amplification is one of the most powerful prognostic indicators for neuroblastoma, the most common solid tumor of young children, and is associated with rapid tumor progression, advanced stage disease and poor outcome. Overexpression of the c-Myc gene is among is among the most frequent events in human cancer and is often associated with more aggressive, poorly differentiated and metastatic types of tumors including those arising in colon, breast, prostate, ovary and skin. Thus, abrogation of Myc function in this class of tumors should have therapeutic benefit without significant side effects of normal tissues that are not dependent on high levels of Myc for survival.

Thus, there exists a need in the art for methods to treat cancer by inhibiting the activity of the c-Myc oncoprotein.

SUMMARY OF THE DISCLOSURE

In various aspects of the disclosure, there is provided a pharmaceutical composition comprising a therapeutically effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In various aspects, there is provided a pharmaceutical composition comprising a therapeutically effective amount of a compound having a structure (I)

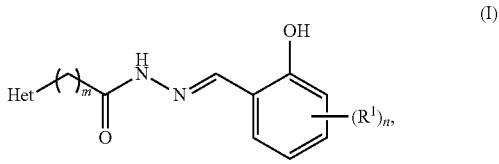

wherein $R^1$ is alkyl, OH, amino, alkoxy, aryl, alkenyl, alkynyl, or alkylenearyl, Het is heteroaryl, and m and n are each independently 0, 1, 2, 3, or 4.

In various aspects, Het is acridinonyl, diazolyl, triazolyl, or tetrazolyl.

In various aspects, Het is substituted with one or more of aryl, alkyl, amino, alkylenecycloheteroalkyl, heteroaryl, and alkyleneamino.

In various aspects, Het is substituted with one or more of $CH_3$, $CH_2CH_3$, $NH_2$, $N(alkyl)_2$, phenyl, oxadiazolyl, $CH_2$amino, $CH_2$tetrahydroisoquinolinyl, and $CH_2$azocanyl.

In various aspects, $R^1$ is $N(alkyl)_2$ or $CH_3$.

In various aspects, m is 0, 1, 2, 3 or 4.

In various aspects, n is 0, 1, 2, 3 or 4.

In various aspects, the pharmaceutical composition further comprises a pharmaceutically acceptable carrier. In various aspects, the pharmaceutically acceptable carrier is selected from the group consisting of Captisol, phosphate buffered saline, water, buffered water, bacteriostatic water, 0.4% saline, and 0.3% glycine.

In various aspects, the pharmaceutical composition further comprises a component selected from the group consisting of a diluent, an excipient, a stabilizer, an anti-microbial agent, a preservative, a suspension agent, and a wetting agent.

In various aspects, the pharmaceutical composition further comprises an anti-cancer agent.

In various aspects of the disclosure, there is provided a method of treating cancer comprising administering to a patient in need thereof a therapeutically effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In various aspects of the disclosure, there is provided a method of treating cancer comprising administering to a patient in need thereof a therapeutically effective amount of a compound having a structure (I)

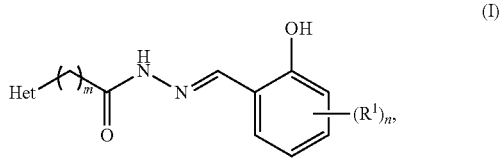

wherein $R^1$ is alkyl, OH, amino, alkoxy, aryl, alkenyl, alkynyl, or alkylenearyl,
Het is heteroaryl,
and m and n are each independently 0, 1, 2, 3, or 4.

In various aspects of the method, the patient has a cancer selected from the group consisting of nueroblastoma, alveolar rhabomyosarcoma, retinoblastoma, small cell lung cancer, melanoma, breast cancer, colon cancer, prostate cancer, ovarian cancer, cervical cancer, lymphoma, and leukemia.

In various aspects, the administered compound inhibits the function of a Myc protein selected from the group consisting of N-Myc, c-Myc, and L-Myc.

In various aspects, the method further comprises administering a therapeutically effective amount of an anti-cancer agent.

In various aspects of the disclosure, there is provided a method of inhibiting a Myc protein comprising the step of contacting a Myc protein with an amount of a compound effective to inhibit the Myc protein, wherein the compound is selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In various aspects of the disclosure, there is provided a method of inhibiting a Myc protein comprising the step of contacting a Myc protein with an amount of a compound effective to inhibit the Myc protein, wherein the compound has a structure (I)

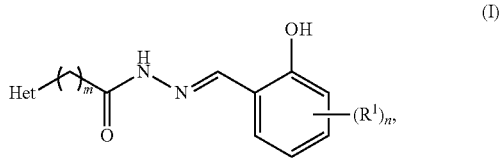

wherein $R^1$ is alkyl, OH, amino, alkoxy, aryl, alkenyl, alkynyl, or alkylenearyl,
Het is heteroaryl,
and m and n are each independently 0, 1, 2, 3, or 4.

In various aspects, the administered compound inhibits the function of a Myc protein selected from the group consisting of N-Myc, c-Myc, and L-Myc.

In various aspects of the disclosure, there is provided a method for treating a condition arising from aberrant Myc activity comprising the step of administering to a patient in need thereof a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7, in an amount effective to treat the condition.

In various aspects of the disclosure, there is provided a method for treating a condition arising from aberrant Myc activity comprising the step of administering to a patient in need thereof a compound having a structure (I)

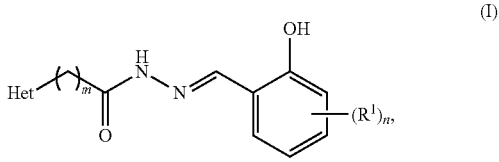

wherein $R^1$ is alkyl, OH, amino, alkoxy, aryl, alkenyl, alkynyl, or alkylenearyl,
Het is heteroaryl,
and m and n are each independently 0, 1, 2, 3, or 4.

In various aspects of the disclosure, there is provided a method of treating an autoimmune disease comprising administering to a patient in need thereof a therapeutically effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In various aspects of the disclosure, there is provided a method of treating an autoimmune disease comprising administering to a patient in need thereof a therapeutically effective amount of a compound having a structure (I)

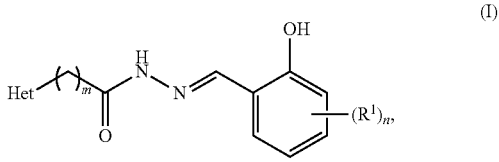

wherein $R^1$ is alkyl, OH, amino, alkoxy, aryl, alkenyl, alkynyl, or alkylenearyl,
Het is heteroaryl,
and m and n are each independently 0, 1, 2, 3, or 4.

In various aspects, the autoimmune disease is selected from the group consisting of Goodpasture's syndrome, Crohn's Disease, Graves' Disease, Lupus erythematosus, Multiple Sclerosis, Psoriasis, Rheumatoid arthritis, and Relapsing polychondritis.

In various aspects, the administered compound inhibits the function of a Myc protein selected from the group consisting of N-Myc, c-Myc, and L-Myc.

In various aspects of the disclosure, there is provided a method of inhibiting cell proliferation comprising contacting a cell with an effective amount of a Myc inhibitor selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In various aspects of the disclosure, there is provided a method of inhibiting cell proliferation comprising contacting a cell with an effective amount of a compound having a structure (I)

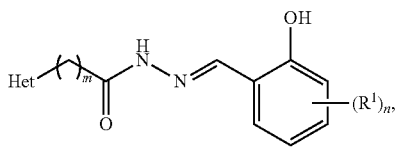

wherein $R^1$ is alkyl, OH, amino, alkoxy, aryl, alkenyl, alkynyl, or alkylenearyl,
Het is heteroaryl,
and m and n are each independently 0, 1, 2, 3, or 4.

In various aspects, the cell is a tumor cell.

In various aspects of the disclosure, there is provided a method of inhibiting tumor cell growth comprising contacting a tumor cell with an effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In various aspects of the disclosure, there is provided a method of inhibiting tumor cell growth comprising contacting a tumor cell with an effective amount of a compound having a structure (I)

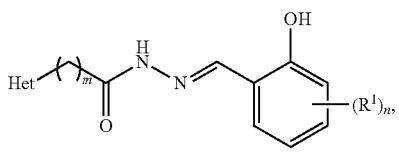

wherein $R^1$ is alkyl, OH, amino, alkoxy, aryl, alkenyl, alkynyl, or alkylenearyl,
Het is heteroaryl,
and m and n are each independently 0, 1, 2, 3, or 4.

In various aspects of the disclosure, there is provided a method of treating an infection comprising administering to a patient in need thereof a therapeutically effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In various aspects of the disclosure, there is provided a method of treating an infection comprising administering to a patient in need thereof a therapeutically effective amount of a compound having a structure (I)

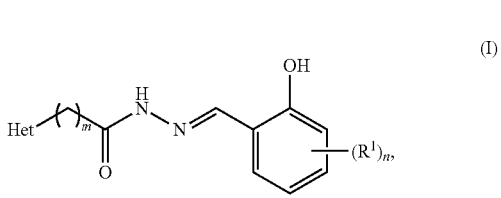

wherein $R^1$ is alkyl, OH, amino, alkoxy, aryl, alkenyl, alkynyl, or alkylenearyl,
Het is heteroaryl,
and m and n are each independently 0, 1, 2, 3, or 4.

Other features and advantages of the present disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION OF THE DISCLOSURE

I. Definitions

Figure 1:
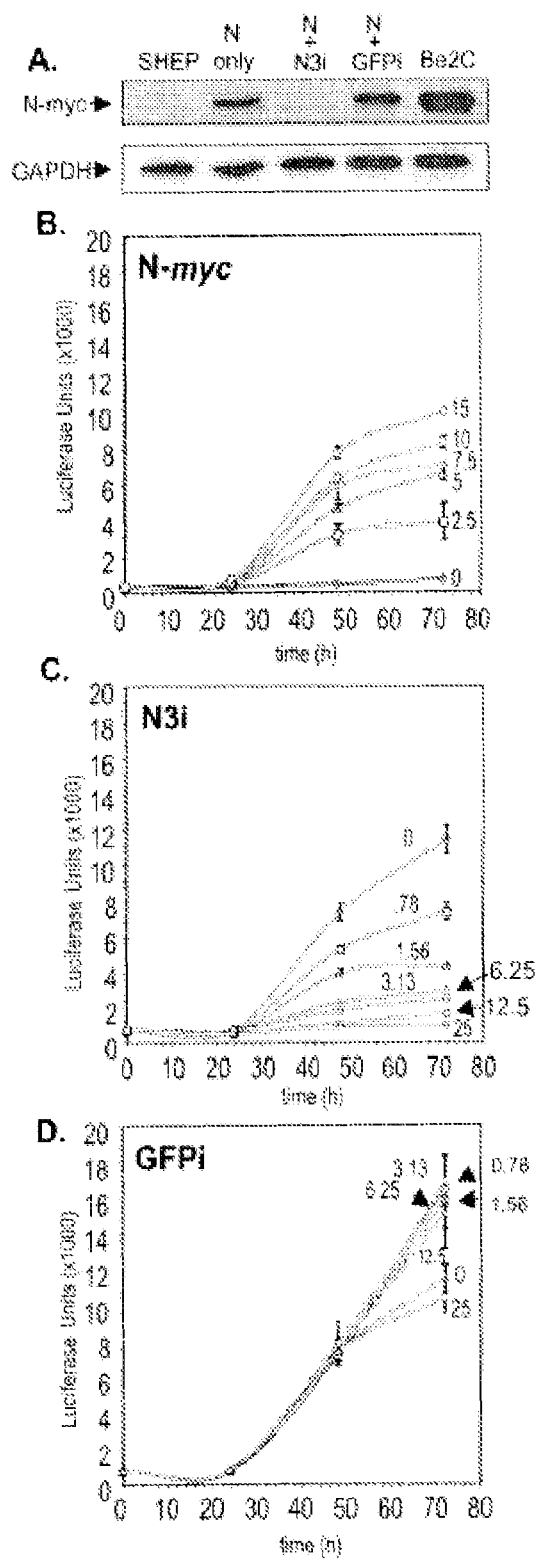
FIG. 1A depicts lysates from SH-EP cells transiently transfected with N-myc expression vector alone or in combination with either the N-myc shRNA construct N3i or GFP shRNA control that were analyzed by western blot for N-myc (upper panel) or GAPDH loading control (lower panel). N3i but not GFP shRNA control completely abrogated N-myc expression.
FIGS. 1B-D illustrate an evaluation of the readout system with SHR6-17 cells. (B) SHR6-17 cells containing the N-myc responsive reporter were transduced with increasing concentrations of N-myc lentivirus for 24, 48 and 72 h in 96-well plates. At each time point, cells were assayed for luciferase activity. Numbers next to each curve correspond to the amount of lentivirus (µl) added per well in a total volume of 200 µl. (C) N-myc shRNA (N3i) but not (D) GFP shRNA (GFPi) blocked N-myc mediated induction of the luciferase reporter. Numbers next to curves indicated the volume of virus added to each well in µl.

It must be noted that as used herein and in the appended claims, the singular forms "a," "and," and "the" include plural referents unless the context clearly dictates otherwise.

A "patient" for the purposes of the present disclosure includes both humans and other animals. Thus the methods are applicable to both human therapy and veterinary applications.

As defined herein, the terms "neoplastic cells", "neoplasia", "tumor", "tumor cells", "cancer" and "cancer cells" refer to cells which exhibit relatively autonomous growth. These cells exhibit an aberrant growth phenotype characterized by a significant loss of control of cell proliferation (i.e., de-regulated cell division). Neoplastic cells can be malignant or benign.

The term "therapeutically effective amount" as used herein refers to an amount of a therapeutic agent to treat, ameliorate, or prevent a disease or condition, or to exhibit a detectable therapeutic or preventative effect. The effect can be detected by, for example, a reduction in tumor size. The effect can also be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. The effective amount for a given situation is determined by routine experimentation and is within the judgment of the clinician. For purposes of the present disclosure, an effective dose will generally be from about 0.01 mg/kg to about 5 mg/kg, or about 0.01 mg/kg to about 50 mg/kg or about 0.05 mg/kg to about 10 mg/kg, or about 0.01 mg/kg to about 10 mg/kg, or about 0.01 mg/kg to about 25 mg/kg, or about 0.01 mg/kg to about 20 mg/kg. or about 0.01 mg/kg to about 0.05 mg/kg, or about 0.01 mg/kg to about 0.1 mg/kg, or about 0.01 mg/kg to about 0.5 mg/kg, or about 0.05 mg/kg to about 20 mg/kg, or about 0.05 mg/kg to about 30 mg/kg, or about 0.05 mg/kg to about 40 mg/kg, or about 0.05 mg/kg to about 50 mg/kg of the compositions of the present disclosure in the individual to which it is administered.

The term "anti-cancer agent" refers to a compound, or a combination of compounds, that kills or slows the reproduction of rapidly multiplying cells.

A "pharmaceutically acceptable salt" is a salt that retains the biological effectiveness of the free acids and bases of the specified compound and that is not biologically or otherwise undesirable. A compound of the disclosure may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present disclosure with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, iso-butyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitro-menzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the administered compound is a base, the desired pharmaceutically acceptable salt is prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the administered compound is an acid, the desired pharmaceutically acceptable salt is prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

II. Compositions

A. Compounds Identified in Screen for Myc Inhibitors

Provided herein are compounds and methods of treatment using compounds having a structure of formula (I):

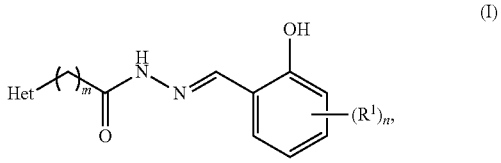

wherein $R^1$ is alkyl, OH, amino, alkoxy, aryl, alkenyl, alkynyl, or alkylenearyl, Het is heteroaryl, and m and n are each independently 0, 1, 2, 3, or 4.

The term "alkyl" used herein refers to a saturated or unsaturated straight or branched chain hydrocarbon group of one to forty carbon atoms, including, but not limited to, methyl, ethyl, n-propyl, isopropyl, n-butyl, isobutyl, tert-butyl, n-hexyl, and the like. Alkyls of one to six carbon atoms are also contemplated. The term "alkyl" includes "bridged alkyl," i.e., a bicyclic or polycyclic hydrocarbon group, for example, norbornyl, adamantyl, bicyclo[2.2.2]octyl, bicyclo[2.2.1] heptyl, bicyclo[3.2.1]octyl, or decahydronaphthyl. Alkyl groups optionally can be substituted, for example, with hydroxy (OH), halide, thiol (SH), aryl, heteroaryl, cycloalkyl, heterocycloalkyl, and amino. It is specifically contemplated that in the compounds described herein the alkyl group consists of 1-40 carbon atoms, preferably 1-25 carbon atoms, preferably 1-15 carbon atoms, preferably 1-12 carbon atoms, preferably 1-10 carbon atoms, preferably 1-8 carbon atoms, and preferably 1-6 carbon atoms.

As used herein, the term "cycloalkyl" refers to a cyclic hydrocarbon group, e.g., cyclopropyl, cyclobutyl, cyclohexyl, and cyclopentyl. "Heterocycloalkyl" is defined similarly as cycloalkyl, except the ring contains one to three heteroatoms independently selected from the group consisting of oxygen, nitrogen, and sulfur. Nonlimiting examples of heterocycloalkyl groups include piperdine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected from the group consisting of alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

The term "alkenyl" used herein refers to a straight or branched chain hydrocarbon group of two to ten carbon atoms containing at least one carbon double bond including, but not limited to, 1-propenyl, 2-propenyl, 2-methyl-1-propenyl, 1-butenyl, 2-butenyl, and the like. The term "cycloalkenyl" refers to a cycloalkyl group having one or more double bonds. "Heterocycloalkenyl" refers to a cycloalkenyl group having one or more heteroatoms (e.g., N, S, O, or combinations thereof).

The term "alkynyl" used herein refers to a straight or branched chain hydrocarbon group of two to ten carbon atoms containing at least one carbon triple bond including, but not limited to, 1-propynyl, 2-propynyl, 1-butynyl, 2-butynyl, and the like.

The term "alkylene" used herein refers to an alkyl group having a substituent. For example, the term "alkylene aryl" refers to an alkyl group substituted with an aryl group. The alkylene group is optionally substituted with one or more substituent previously listed as an optional alkyl substituent. For example, an alkylene group can be —CH$_2$CH$_2$— or —CH$_2$—.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, OCF$_3$, NO$_2$, CN, NC, OH, alkoxy, amino, CO$_2$H, CO$_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. As used herein, heteroaryl is interchangeably used with the term "Het." In some cases, "Het" is selected from the group consisting of

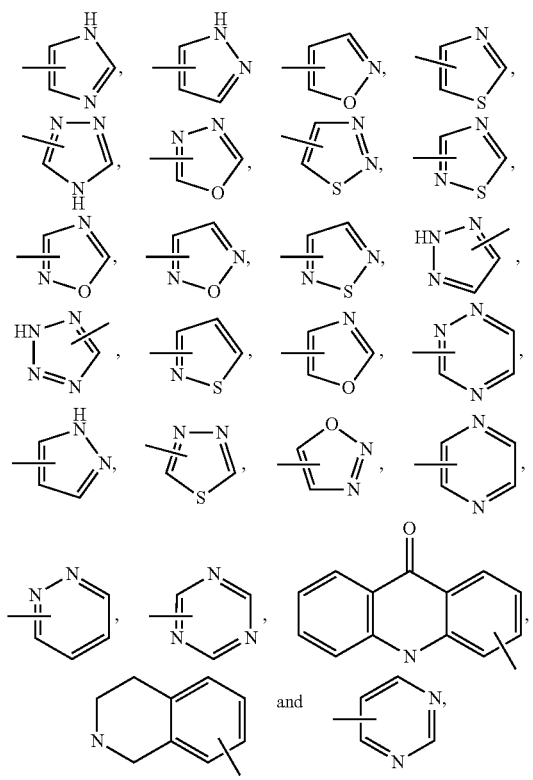

or a substituted moiety thereof. In some cases, Het is substituted with one or more of alkyl, NH$_2$, NHaklyl, N(alkyl)$_2$, heterocycloalkyl, aryl, and another heteroaryl group.

The term "alkoxy" used herein refers to straight or branched chain alkyl group covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "amino" as used herein refers to —NR$_2$, where R is independently hydrogen, optionally substituted alkyl, optionally substituted heteroalkyl, optionally substituted cycloalkyl, optionally substituted heterocycloalkyl, optionally substituted aryl or optionally substituted heteroaryl. Non-limiting examples of amino groups include NH$_2$, NH(CH$_3$), N(CH$_3$)$_2$, N(Et)$_2$, and N(CH$_2$CH$_2$CH$_3$)$_2$. In some cases, R is independently hydrogen or alkyl.

As used herein, a substituted group is derived from the unsubstituted parent structure in which there has been an exchange of one or more hydrogen atoms for another atom or group. A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (B) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from:

(i) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (ii) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from:

(a) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (b) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl.

In an embodiment, the disclosure provides a pharmaceutical composition comprising a therapeutically effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In an embodiment, the disclosure provides a pharmaceutical composition comprising a compound having a structure (I)

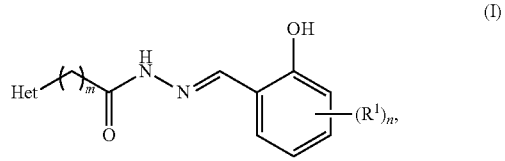

wherein R$^1$ is alkyl, OH, amino, alkoxy, aryl, alkenyl, alkynyl, or alkylenearyl, Het is heteroaryl, and m and n are each independently 0, 1, 2, 3, or 4.

In an embodiment, the disclosure provides a pharmaceutical composition comprising a compound of formula (I) where Het is acridinonyl, diazolyl, triazolyl, or tetrazolyl.

In an embodiment, the disclosure provides a pharmaceutical composition comprising a compound of formula (I), where Het is substituted with one or more of aryl, alkyl, amino, alkylenecycloheteroalkyl, heteroaryl, and alkyleneamino.

In an embodiment, the disclosure provides a pharmaceutical composition comprising a compound of formula (I), where Het is substituted with one or more of CH$_3$, CH$_2$CH$_3$, NH$_2$, N(alkyl)$_2$, phenyl, oxadiazolyl, CH$_2$amino, CH$_2$tetrahydroisoquinolinyl, and CH$_2$azocanyl.

In an embodiment, the disclosure provides a pharmaceutical composition comprising a compound of formula (I), where R$^1$ is N(alkyl)$_2$ or CH$_3$.

In an embodiment, the disclosure provides a pharmaceutical composition comprising a compound of formula (I), where m is 0, 1, 2, 3, or 4.

In an embodiment, the disclosure provides a pharmaceutical composition comprising a compound of formula (I), where n is 0, 1, 2, 3, or 4.

In an embodiment, the disclosure provides a pharmaceutical composition comprising a compound selected from the group consisting of N77A7, Compound 1, Compound 2, Compound 3, Compound 4, Compound 5, Compound 6, and Compound 7.

In an embodiment, the disclosure provides a pharmaceutical composition of the compounds described herein further comprising a pharmaceutically acceptable carrier. In an embodiment, the pharmaceutically acceptable carrier is selected from the group consisting of Captisol, phosphate buffered saline, water, buffered water, bacteriostatic water, 0.4% saline, and 0.3% glycine. In an embodiment, pharmaceutical composition further comprises a component selected from the group consisting of a diluent, an excipient, a stabilizer, an anti-microbial agent, a preservative, a suspension agent, and a wetting agent. In an embodiment, pharmaceutical composition further comprises an anti-cancer agent.

In an embodiment, the pharmaceutical composition comprises N77A7 and Captisol.

A screen for small molecules that inhibit the growth of Myc-expressing cells identified a panel of 18 compounds that preferentially targeted Myc-expressing cells. The screen is described in Examples 1, 2, and 3. SH-EP neuroblastoma cells were stably transfected with a luciferase reporter gene under the control of a minimal heat shock protein promoter that contained 6 copies of the E-box sequence needed for N-myc specific transactivation and selected with G418, resulting in the identification of clone SHR6-17, the readout cell line. The 18 compounds identified in the screening and filtering process are shown in Table 1. 260 analogs of N77A7 were selected from several commercially available libraries of small molecules based on the structural similarities with N77A7. The compounds were also screened for the ability to permanently suppress proliferation and induce senescence in cells from melanoma lines SK-Mel-19 and SK-Mel-103. Seven N77A7 analogs were identified as having IC50 values lower than that of N77A7. Table 2 shows the structures of the N77A7 analogs with Myc inhibition activity.

TABLE 1

Compounds Identified in Screen for Myc Inhibitors

| Compound | Class* | Structure | ID50(uM) HO-null | ID50(uM) HO—N-myc | ID50(uM) HO-c-myc | Myc Index** N | C |
|---|---|---|---|---|---|---|---|
| N423F7 | U | 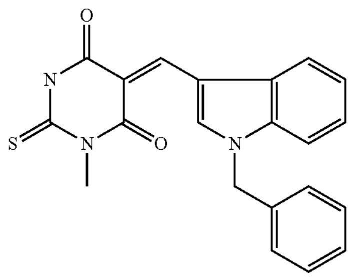 [SMILES: CN1C(=O)/C(=C\c2cn(Cc3ccccc3)c3ccccc23)C(=O)NC1=S] | 1985 | 120 | 89.1 | 17 | 22 |
| N6008 | I | 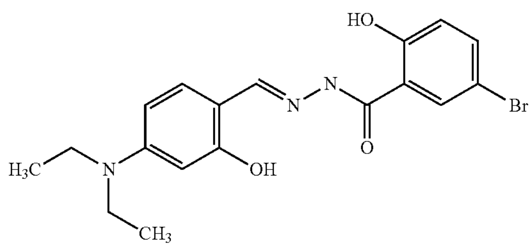 [SMILES: CCN(CC)c1ccc(/C=N/NC(=O)c2cc(Br)ccc2O)c(O)c1] | >25 | 2.34 | 2.32 | >11 | >11 |
| N4G6 | VII | 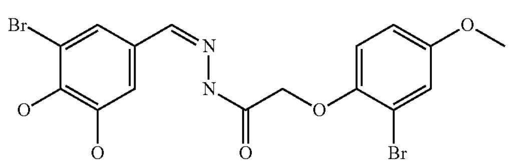 [SMILES: COc1ccc(OCC(=O)N/N=C\c2cc(O)c(O)c(Br)c2)c(Br)c1] | >100 | 10.2 | 32.6 | >10 | >3 |
| N49C4 | U | 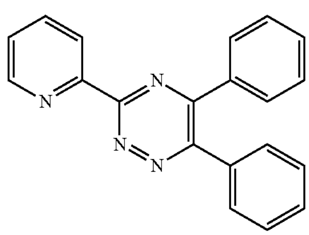 [SMILES: c1ccc(-c2nnc(-c3ccccn3)nc2-c2ccccc2)cc1] | 159 | ~728 | 19.6 | 8.1 | 0.22 |
| N171H10 | V | 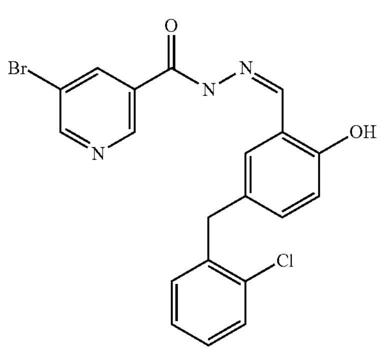 [SMILES: O=C(N/N=C\c1cc(Cc2ccccc2Cl)ccc1O)c1cncc(Br)c1] | >25 | 4 | 2.6 | >6 | >10 |

TABLE 1-continued

Compounds Identified in Screen for Myc Inhibitors

| Compound | Class* | Structure | ID50(uM) HO-null | ID50(uM) HO—N-myc | ID50(uM) HO-c-myc | Myc Index** N | Myc Index** C |
|---|---|---|---|---|---|---|---|
| N117E2 | IX | 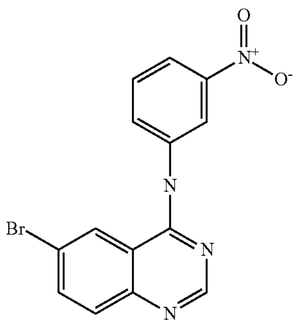 [SMILES: O=[N+]([O-])c1cccc(Nc2ncnc3ccc(Br)cc23)c1] | >50 | 8.8 | 7.49 | >6 | >7 |
| N18C5 | U | 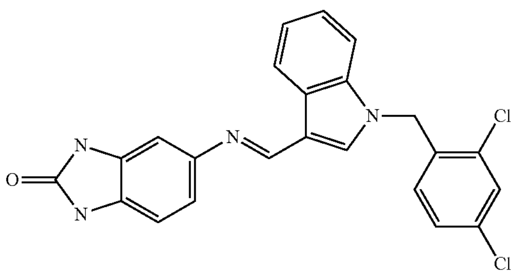 [SMILES: O=c1[nH]c2ccc(/N=C/c3cn(Cc4ccc(Cl)cc4Cl)c4ccccc34)cc2[nH]1] | >100 | 16 | >100 | >6 | 1 |
| N117G10 | IX | 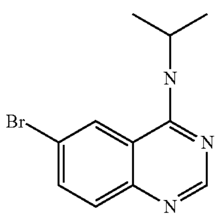 | 28.2 | 4.58 | 6.27 | 6 | 4.5 |
| N147G5 | VIII | 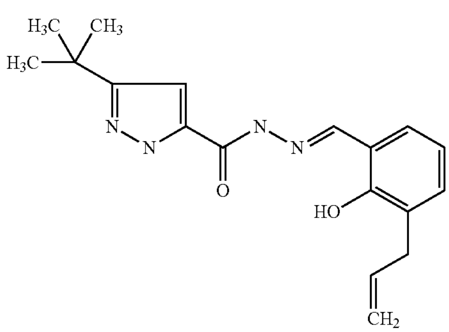 [SMILES: C=CCc1cccc(/C=N/NC(=O)c2cc(C(C)(C)C)n[nH]2)c1O] | >25 | 5 | 4.2 | >5 | >6 |
| N269D8 | U | 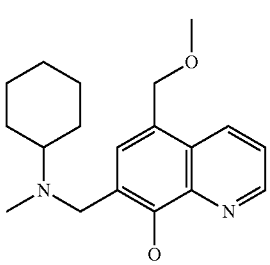 [SMILES: COCc1cc(CN(C)C2CCCCC2)c(O)c2ncccc12] | 4.52 | 0.85 | 0.72 | 5.3 | 6.3 |

TABLE 1-continued

Compounds Identified in Screen for Myc Inhibitors

| Compound | Class* | Structure | ID50(uM) HO-null | ID50(uM) HO—N-myc | ID50(uM) HO-c-myc | Myc Index** N | C |
|---|---|---|---|---|---|---|---|
| N47E10 | VIII | 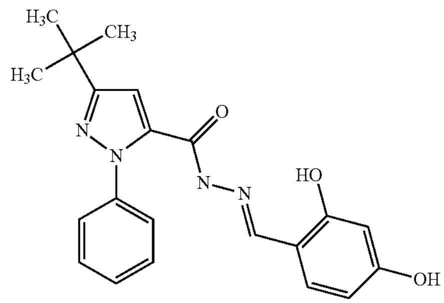 [SMILES: CC(C)(C)c1cc(C(=O)N/N=C/c2ccc(O)cc2O)n(-c2ccccc2)n1] | 7.21 | 1.44 | 2.54 | 5 | 2.8 |
| N144G3 | IV | 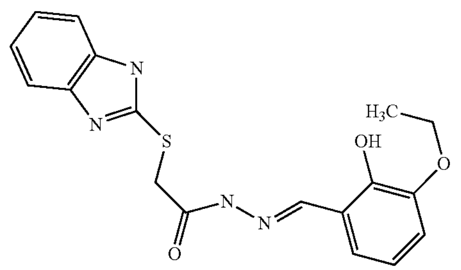 [SMILES: CCOc1cccc(/C=N/NC(=O)CSc2nc3ccccc3[nH]2)c1O] | 83.2 | 17.8 | 25.8 | 4.7 | 3.22 |
| N77A7 | U | 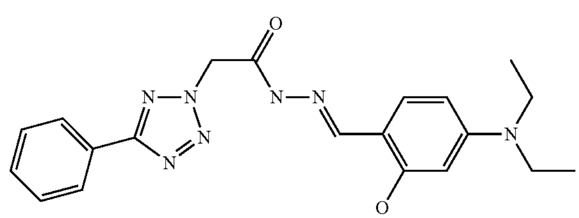 [SMILES: CCN(CC)c1ccc(/C=N/NC(=O)Cn2nnc(-c3ccccc3)n2)c(O)c1] | 3.64 | 0.77 | 4.7 | 4.5 | 0.8 |
| N103A8 | II | 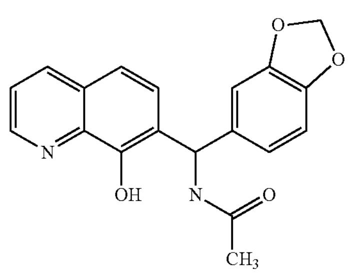 [SMILES: CC(=O)NC(c1ccc2c(c1)OCO2)c1ccc2cccnc2c1O] | 7.57 | 1.69 | 1.62 | 4.5 | 4.7 |
| N147A7 | VIII | 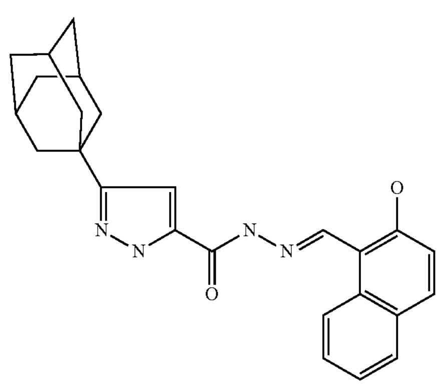 [SMILES: O=C(N/N=C/c1c(O)ccc2ccccc12)c1cc(C23CC4CC(CC(C4)C2)C3)n[nH]1] | 5.12 | 1.9 | 3.94 | 2.7 | 1.3 |

TABLE 1-continued

Compounds Identified in Screen for Myc Inhibitors

| Compound | Class* | Structure | ID50(uM) HO-null | ID50(uM) HO—N-myc | ID50(uM) HO-c-myc | Myc Index** N | Myc Index** C |
|---|---|---|---|---|---|---|---|
| N121F3 | III | 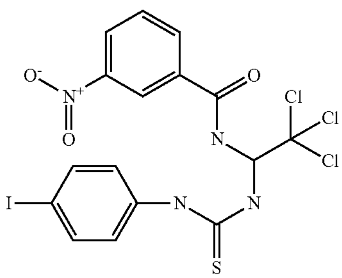 [SMILES: O=C(NC(NC(=S)Nc1ccc(I)cc1)C(Cl)(Cl)Cl)c1cccc([N+](=O)[O-])c1] | 23.48 | 9.7 | 11.3 | 2.4 | 2.1 |
| N6A8 | U | 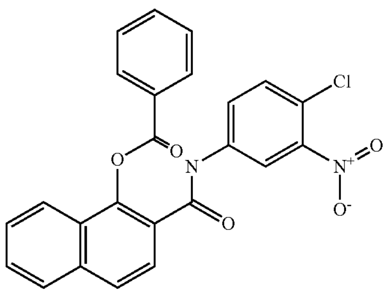 [SMILES: O=C(Oc1c(C(=O)Nc2ccc(Cl)c([N+](=O)[O-])c2)ccc2ccccc12)c1ccccc1] | 21.1 | 9.71 | 8.86 | 2.2 | 2.4 |
| N4D2 | VII | 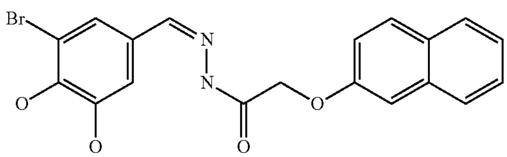 [SMILES: O=C(COc1ccc2ccccc2c1)N/N=C\c1cc(O)c(O)c(Br)c1] | >100 | 88 | 33.8 | >1.1 | >3 |

*Unique Structure

**Myc Index is calculated by dividing the ID50 of a compound in HO-null cells by the ID50 of that compound in either HO—N-myc (N) or HO-c-myc (C) cells.

TABLE 2

N77A7 analogs with myc inhibition activity

| Compound | Structure |
|---|---|
| N77A7 | 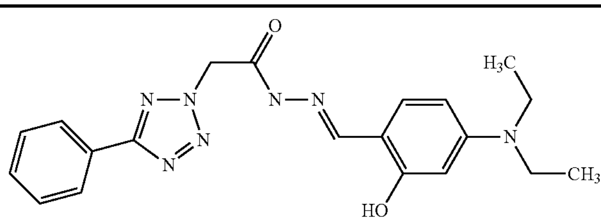 |
| Compound 1 | 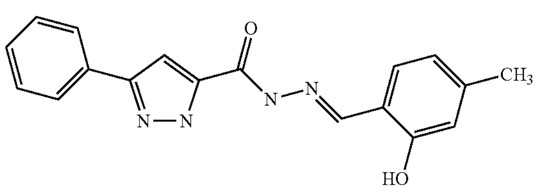 [SMILES: Cc1ccc(/C=N/NC(=O)c2cc(-c3ccccc3)n[nH]2)c(O)c1] |

TABLE 2-continued
N77A7 analogs with myc inhibition activity
| Compound | Structure |
|---|---|
| Compound 2 | 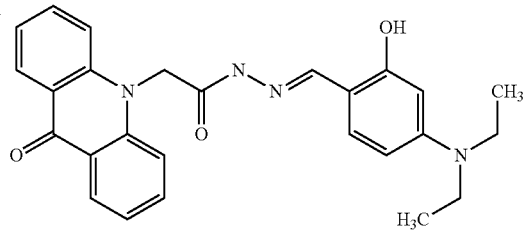 [SMILES: CCN(CC)c1ccc(/C=N/NC(=O)Cn2c3ccccc3c(=O)c3ccccc32)c(O)c1] |
| Compound 3 | 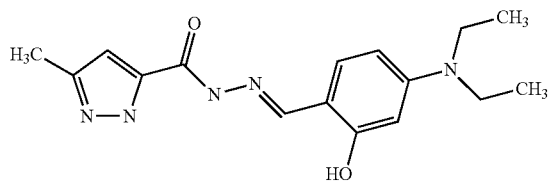 [SMILES: CCN(CC)c1ccc(/C=N/NC(=O)c2cc(C)n[nH]2)c(O)c1] |
| Compound 4 | 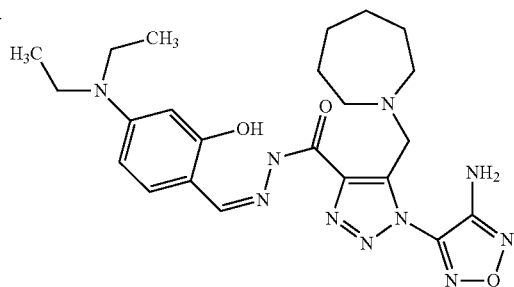 |
| Compound 5 | 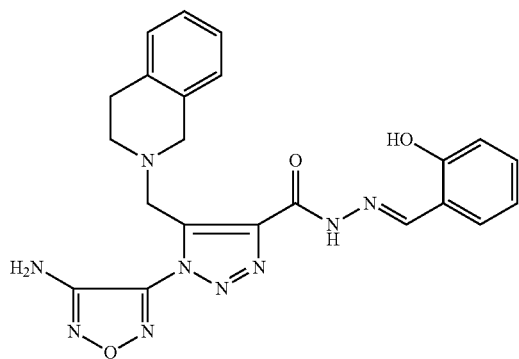 [SMILES: Nc1nonc1-n1nnc(C(=O)N/N=C/c2ccccc2O)c1CN1CCc2ccccc2C1] |
| Compound 6 | 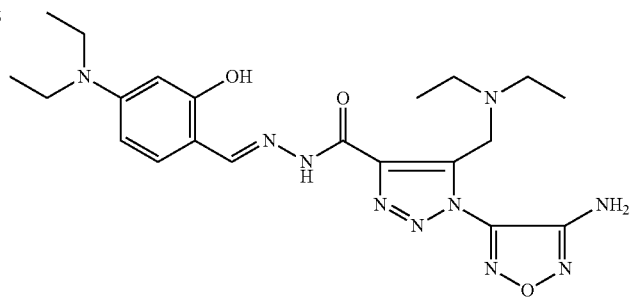 |

TABLE 2-continued

N77A7 analogs with myc inhibition activity

| Compound | Structure |
|---|---|
| Compound 7 | 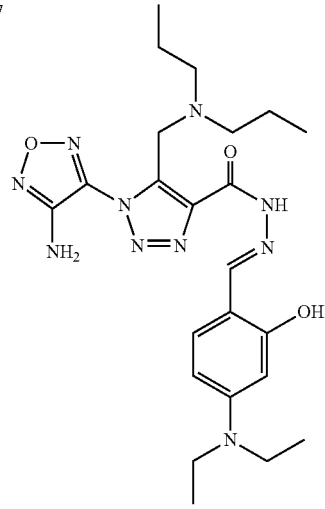 |

Pharmaceutical Compositions

The compounds used in the practice of a method of the disclosure are, in various aspects, formulated into pharmaceutical compositions comprising a carrier suitable for the desired delivery method. Suitable carriers include any material which, when combined with the compounds, retains the anti-tumor function of the compound and is nonreactive with the subject's immune systems. Examples include, but are not limited to, any of a number of standard pharmaceutical carriers such as sterile phosphate buffered saline solutions, bacteriostatic water, and Captisol®. A variety of aqueous carriers are used and optionally include other proteins for enhanced stability, such as albumin, lipoprotein, globulin. The formulations to be used for in vivo administration must be sterile. This is readily accomplished by filtration through sterile filtration membranes.

Compositions of the present disclosure in various aspects, are in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant disclosure.

Therapeutic formulations of the compound are prepared for storage by mixing the compound having the desired degree of purity with optional physiologically acceptable carriers, excipients, bulking agents or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers, antioxidants, preservatives, low molecular weight (less than about 10 residues) polypeptides, proteins, hydrophilic polymers, amino acids, monosaccharides, disaccharides, and other carbohydrates, chelating agents, sugars s, salt-forming counter-ions, metal complexes, and/or non-ionic surfactants.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. In certain aspects, the oil or fatty acid is non-volatile, including natural or synthetic oils, fatty acids, mono-, di- or tri-glycerides.

i. Stabilizers

In a particular embodiment of the present compositions, a stabilizer (or a combination of stabilizers) is added to the formulation. The term "stabilizer" means an excipient capable of preventing aggregation or other physical degradation, as well as chemical degradation (for example, autolysis, deamidation, oxidation, etc.) in an aqueous and solid state. Stabilizers that are conventionally employed in pharmaceutical compositions include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, polyhydroxy compounds, including polysaccharides such as dextran, starch, hydroxyethyl starch, cyclodextrins, N-methyl pyrollidene, cellulose and hyaluronic acid, sodium chloride, [Carpenter et al., Develop. Biol. Standard 74:225, (1991)]. In one embodiment, the stabilizer is incorporated in a concentration of about 0% to about 40% w/v. In another embodiment, the stabilizer is incorporated in a concentration of at least 0.5, 1, 2, 3, 4, 5, 6, 7, 8, 9, 10, 11, 12, 13, 14, 15, 16, 17, 18, 19, 20, 30, or 40% w/v. In another embodiment, the stabilizer is incorporated in a concentration of about 1, 2, 3, 4, 5, 6, 7, 8, 9% to about 10% w/v. In still another embodiment, the stabilizer is incorporated in a concentration of about 2% to about 6% w/v. In yet another embodiment, the stabilizer is incorporated in a concentration of about 4% w/v. In yet another embodiment, the stabilizer is incorporated in a concentration of about 6% w/v.

If desired, the formulations also include appropriate amounts of bulking and osmolarity regulating agents suitable for forming a lyophilized "cake." Bulking agents may be either crystalline (for example, mannitol, glycine) or amorphous (for example, sucrose, polymers such as dextran, polyvinylpyrolidone, carboxymethylcellulose). Other exemplary bulking agents include lactose, sorbitol, trehalose, or xylitol. In one embodiment, the bulking agent is sucrose. In a further embodiment, the bulking agent is incorporated in a concentration of about 0% to about 10% w/v. In another embodiment, the bulking agent is incorporated in a concentration of at least 0.2, 0.5, 0.7, 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5% w/v. In a yet further embodiment in a concentration of about 1, 1.5, 2.0, 2.5, 3.0, 3.5, 4.0, 4.5% to 5.0% w/v, to produce a mechanically and pharmaceutically stable and elegant cake. In another embodiment, the sucrose concentration is 4% w/v. In another embodiment, the sucrose concentration is 6% w/v.

ii. Buffers

Organic acids, phosphates and Tris have been employed routinely as buffers. The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration. The buffer system present in the formulation is selected to be physiologically compatible and to maintain a desired pH.

Several factors need to be considered when choosing a buffer. First and foremost, the buffer species and its concentration need to be defined based on its pKa and the desired formulation pH. Equally important is to ensure that the buffer is compatible with the protein drug, other formulation excipients, and does not catalyze any degradation reactions. Recently, polyanionic carboxylate buffers such as citrate and succinate have been shown to form covalent adducts with the side chain residues of proteins. A third important aspect to be considered is the sensation of stinging and irritation the buffer may induce. For example, citrate is known to cause stinging upon injection (Laursen T, et al., Basic Clin. Pharmacol. Toxicol., 98(2): 218-21 (2006)). The potential for stinging and irritation is greater for drugs that are administered via the SC or IM routes, where the drug solution remains at the site for a relatively longer period of time than when administered by the IV route where the formulation gets diluted rapidly into the blood upon administration. For formulations that are administered by direct IV infusion, the total amount of buffer (and any other formulation component) needs to be monitored. For example, it has been reported that potassium ions administered in the form of the potassium phosphate buffer, can induce cardiovascular effects in a patient (Hollander-Rodriguez J C, et al., Am. Fam. Physician, 73(2): 283-90 (2006)).

The pH buffering compound may be present in any amount suitable to maintain the pH of the formulation at a predetermined level. In another embodiment, when the pH buffering agent is an acetate buffer, the concentration of the amino acid is between 0.1 mM and 1000 mM (1 M). In one embodiment, the pH buffering agent is at least 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, or 900 mM. In another embodiment, the concentration of the pH buffering agent is between 1, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, or 90 mM and 100 mM. In still another embodiment, the concentration of the pH buffering agent is between 5, 6, 7, 8, 9, 10, 11, 12, 13, 14, 15, 16, 17, 18, 19, 20, 30, or 40 mM and 50 mM. In yet another embodiment, the concentration of the pH buffering agent is 10 mM.

Other exemplary pH buffering agents used to buffer the formulation as set out herein include, but are not limited to glycine, glutamate, succinate, phosphate, acetate, and aspartate.

iii. Antioxidants

Oxidation of compounds arises from a number of different sources. Beyond the addition of specific antioxidants, the prevention of oxidative damage involves the careful control of a number of factors throughout the manufacturing process and storage of the product such as atmospheric oxygen, temperature, light exposure, and chemical contamination. The most commonly used pharmaceutical antioxidants are reducing agents, oxygen/free-radical scavengers, or chelating agents. Antioxidants in therapeutic formulations must be water-soluble and remain active throughout the product shelf-life. Reducing agents and oxygen/free-radical scavengers work by ablating active oxygen species in solution. Chelating agents such as EDTA can be effective by binding trace metal contaminants that promote free-radical formation.

iv. Amino Acids

Amino acids have found versatile use in therapeutic formulations as buffers, bulking agents, stabilizers and antioxidants. Histidine and glutamic acid are employed to buffer protein formulations in the pH range of 5.5-6.5 and 4.0-5.5 respectively. The imidazole group of histidine has a pKa=6.0 and the carboxyl group of glutamic acid side chain has a pKa of 4.3 which makes them suitable for buffering in their respective pH ranges. Acetate, the most commonly used buffer in the acidic pH range of 4.0-5.5, sublimates during lyophilization and hence should not be used in freeze-dried formulations. Glutamic acid is particularly useful in such cases (e.g., Stemgen®). Histidine is commonly found in marketed protein formulations (e.g., Xolair®, Herceptin®, Recombinate®). It provides a good alternative to citrate, a buffer known to sting upon injection.

v. Preservatives

Preservatives are necessary when developing multi-use parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol.

v. Surfactants

Exemplary surfactants include anionic, cationic, nonionic, zwitterionic, and amphoteric surfactants including surfactants derived from naturally occurring amino acids. Anionic surfactants include, but are not limited to, sodium lauryl sulfate, dioctyl sodium sulfosuccinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. In another embodiment, surfactants include lauromacrogol 400, polyoxyl 40 stearate, polyoxyethylene hydrogenated castor oil 10, 40, 50 and 60, glycerol monostearate, polysorbate 40, 60, 65 and 80, soy lecithin and other phospholipids such as DOPC, DMPG, DMPC, and DOPG; sucrose fatty acid ester, methyl cellulose and carboxymethyl cellulose. Compositions comprising these surfactants, either individually or as a mixture in different ratios, are therefore further provided. In one embodiment, the surfactant is incorporated in a concentration of about 0% to about 5% w/v. In another embodiment, the surfactant is incorporated in a concentration of at least 0.001, 0.002, 0.005, 0.007, 0.01, 0.05, 0.1, 0.2, 0.3, 0.4, 0.5, 0.6, 0.7, 0.7, 0.8, 0.9, 1.0, 1.5, 2.0, 2.5, 3.0, 3.5, 4.0, or 4.5% w/v. In another embodiment, the surfactant is incorporated in a concentration of about 0.001% to about 0.5% w/v. In still another embodiment, the surfactant is incorporated in a concentration of about 0.004, 0.005, 0.007, 0.01, 0.05, or 0.1% w/v to about 0.2% w/v. In yet another embodiment, the surfactant is incorporated in a concentration of about 0.01% to about 0.1% w/v.

vi. Sustained Release Formulations

Sustained-release preparations are also contemplated. Suitable examples of sustained-release preparations include semipermeable matrices of solid hydrophobic polymers containing the compound, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid.

The instant compositions contemplated also include those that are in, for example, micelles or liposomes, or some other encapsulated form, or those that are administered in an extended release form to provide a prolonged storage and/or delivery effect. Therefore, the pharmaceutical formulations and medicaments include those compressed into pellets or cylinders and implanted intramuscularly or subcutaneously as depot injections or as implants such as stents. Such implants optionally employ known inert materials such as silicones and biodegradable polymers.

The active ingredients are, in various aspects, entrapped in a microcapsule. Encapsulated compositions are prepared, in various aspects, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The compounds of the present disclosure may also be administered via liposomes, which are small vesicles composed of various types of lipids and/or phospholipids and/or surfactant which are useful for delivery of a drug (such as the compounds disclosed herein and, optionally, a chemotherapeutic agent). Liposomes include emulsions, foams, micelles, insoluble monolayers, phospholipid dispersions, lamellar layers and the like, and can serve as vehicles to target the compounds to a particular tissue as well as to increase the half life of the composition. A variety of methods are available for preparing liposomes, as described in, e.g., U.S. Pat. Nos. 4,837,028 and 5,019,369, which patents are incorporated herein by reference.

Liposomes containing the compounds are prepared by methods known in the art, such as described in Epstein et al., Proc. Natl. Acad. Sci. USA 82: 3688 (1985); Hwang et al., Proc. Natl Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent (such as Doxorubicin) is optionally contained within the liposome [see, e.g., Gabizon et al., J. National Cancer Inst. 81(19): 1484 (1989)].

vii. Dosage

Compositions of the disclosure are administered to a mammal already suffering from, or predisposed to, cancer in an amount sufficient to prevent or at least partially arrest the development of cancer. An amount adequate to accomplish this is defined as a "therapeutically effective dose." Effective amounts of a compound will vary and depend on the severity of the disease and the weight and general state of the patient being treated, but generally range from about 1.0 µg/kg to about 100 mg/kg body weight, or about 10 µg/kg to about 30 mg/kg, with dosages of from about 0.1 mg/kg to about 10 mg/kg or about 1 mg/kg to about 10 mg/kg per application being more commonly used. For example, about 10 µg/kg to 5 mg/kg or about 30 µg/kg to 1 mg/kg of compound is an initial candidate dosage for administration to the patient, whether, for example, by one or more separate administrations, or by continuous infusion. Administration is daily, on alternating days, weekly or less frequently, as necessary depending on the response to the disease and the patient's tolerance of the therapy. Maintenance dosages over a longer period of time, such as 4, 5, 6, 7, 8, 10 or 12 weeks or longer may be needed until a desired suppression of disease symptoms occurs, and dosages may be adjusted as necessary. The progress of this therapy is easily monitored by conventional techniques and assays.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant disclosure.

The concentration of the compound in these compositions varies as needed, i.e., from less than about 10%, usually at least about 25% to as much as 75% or 90% by weight and will be selected primarily by fluid volumes, viscosities, etc., in accordance with the particular mode of administration selected. Actual methods for preparing orally, topically and parenterally administrable compositions will be known or apparent to those skilled in the art and are described in detail in, for example, Remington's Pharmaceutical Science, 19th ed., Mack Publishing Co., Easton, Pa. (1995).

Single or multiple administrations of the compositions can be carried out with the dose levels and pattern being selected by the treating physician. For the prevention or treatment of disease, the appropriate dosage of antibody will depend on the type of disease to be treated, as defined above, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. The composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to prevent, ameliorate, or treat the Myc-mediated disease, condition or disorder, particularly to treat cancer cells. Such amount is preferably below the amount that is toxic to the host or renders the host significantly more susceptible to infections.

viii. Formulations with Additional Active Components

Formulations are also contemplated wherein more than one active compound is included as necessary for the particular indication being treated. In one aspect, different compounds which have complementary activities that do not adversely affect each other are contemplated. Such molecules are suitably present in combination in amounts that are effective for the purpose intended. For example, in cancer, the compound is optionally given in conjunction with an anticancer agent. The effective amount of such other agents depends on the amount of compound present in the formulation, the type of disease, condition or disorder or treatment, and other factors discussed above. These are generally used in the same dosages and with administration routes as used hereinbefore.

In some embodiments, an anti-cancer agent is co-administered or co-formulated with N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and/or Compound 7 wherein the anti-cancer agent is selected from the group consisting of Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin;

hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; Rh retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In particular examples, such anti-cancer agents are administered in combination with a Myc inhibitor of the disclosure.

In some embodiments, an antibiotic is co-administered or co-formulated with N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and/or Compound 7 wherein the antibiotic is selected from the group consisting of Amikacin, Gentamicin, Kanamycin, Neomycin, Netilmicin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Telavancin, Clindamycin, Lincomycin, Daptomycin, Azithromycin, Clarithromycin, Dirithromycin, Erythromycin, Roxithromycin, Troleandomycin, Telithromycin, Spectinomycin, Aztreonam, Furazolidone, Nitrofurantoin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfonamidochrysoidine, Sulfacetamide, Sulfadiazine, Silver sulfadiazine, Sulfamethizole, Sulfamethoxazole, Sulfanilimide, Sulfasalazine, Sulfisoxazole, Trimethoprim, Trimethoprim-Sulfamethoxazole, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin, Rifabutin, Rifapentine, Streptomycin, Arsphenamine, Chloramphenicol, Fosfomycin, Fusidic acid, Linezolid, Metronidazole, Mupirocin, Platensimycin, Quinupristin/Dalfopristin, Rifaximin, Thiamphenicol, Tigecycline, and Tinidazole.

In some embodiments, an autoimmune disease therapeutic is co-administered or co-formulated with N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and/or Compound 7 wherein the autoimmune disease therapeutic is selected from the group consisting of glucocorticoids, cytostatics (e.g., cyclophosphamide, nitrosoureas, platinum compounds, dactinomycin, anthracyclines, mitomycin C, bleomycin, mithramycin), antimetabolites (e.g., methotrexate, azathioprine, mercaptopurine), antibodies (e.g., Muromonab-CD3, daclizumab, basiliximab), ciclosporin, tacrolimus, sirolimus, IFN-β, IFN-γ, opioids, TNF binding proteins (e.g., infliximab, etanercept, adalimumab), mycophenolic acid, fingolimod, myriocin, and ciclosporin.

C. Articles of Manufacture

In another embodiment of the disclosure, an article of manufacture, optionally produced in a kit, containing materials useful for the treatment of the diseases, disorders or conditions described above is provided, including for treatment of cancer. The article of manufacture comprises a container and a label. Suitable containers include, for example, bottles, vials, syringes, and test tubes. The containers are optionally formed from a variety of materials such as glass or plastic. The container holds a composition which is effective for treating the condition and has a sterile access port (for example the container may be an intravenous solution bag or a vial having a stopper pierceable by a hypodermic injection needle). The active agent in the composition is the compound of the disclosure. The label on, or associated with, the container indicates that the composition is used for treating the condition of choice. The article of manufacture optionally further comprises a second container comprising a pharmaceutically-acceptable buffer, such as phosphate-buffered saline, Ringer's solution and dextrose solution. It optionally further includes other materials desirable from a commercial and user standpoint, including other buffers, diluents, filters, needles, syringes, and package inserts with instructions for use.

D. Routes of Administration

The compound is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the compound is suitably administered by pulse infusion, particularly with declining doses of the compound. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g., through a catheter placed close to the desired site.

III. Cancers Associated with Myc Gene Amplification

N-myc gene amplification is one of the most powerful prognostic indicators for neuroblastoma, the most common solid tumor of young children, and is associated with rapid tumor progression, advanced stage disease and poor outcome. While the mechanisms by which amplification of N-myc influences the prognosis of neuroblastoma are not well defined, direct evidence for the critical role of N-myc in this disease has come from a transgenic mouse model of neuroblastoma developed by Weiss et al. in which expression of the human N-myc oncogene was targeted specifically to neuroectodermal cells using the tyrosine hydroxylase promoter. These mice develop a murine equivalent of human neuroblastoma that closely reflects the genotypic and phenotypic characteristics of the human disease, including the expression of neuroblastoma-associated markers and syntenic chromosomal changes. In addition, tumorigenesis correlates with N-myc gene dose such that the tumor incidence in mice hemizygous for the human N-myc transgene is ~30% whereas the incidence in homozygous mice is 100%. When these mice were treated systemically with N-myc antisense oligonucleotides, there was a marked decrease in tumor incidence in hemizygous mice and in tumor size among both homozygous and hemizygous mice, providing proof of principle evidence that targeting N-myc has therapeutic potential. In addition to neuroblastoma, aberrant expression of N-myc has been found in alveolar rhabdomyosarcoma, retinoblastoma and small cell lung cancer. Thus, in some embodiments, the cancer treated by the disclosed methods and compositions includes neuroblastoma, retinoblastoma, rhabdomyosarcoma, and/or small cell lung cancer.

Overexpression of the c-Myc gene is among is among the most frequent events in human cancer and is often associated with more aggressive, poorly differentiated and metastatic types of tumors including those arising in colon, breast, prostate, ovary and skin. Elevated expression of c-Myc in human cancers can be maintained through several mechanisms, including genomic rearrangements (e.g., Burkitt's lymphoma), amplification of the c-Myc-containing locus of chromosome 8 (e.g., breast, colon, prostate, cervical cancers and melanomas), transcriptional hyperactivation of the c-Myc gene (e.g., colon cancer), enhanced cap-dependent and cap-independent translation rates of c-Myc mRNA and enhanced protein stability. In transgenic mouse models of cancer, overexpression of c-myc under tissue-specific inducible promoters resulted in tumor formation. Conversely, abolishing c-myc expression in transgenic mouse tumors by shutting down the inducible promoter resulted in complete regression of the tumor in the vast majority of cases with either brief or sustained inhibition of the inducible promoter depending on the cell type. In different models, regression was accompanied by a combination of the following: cell cycle arrest or apoptosis, senescence, vascular degeneration and/or differentiation. Taken together, these data suggest that Myc overexpressing tumors are dependent on high levels of c-Myc, implying the importance of this oncogene for tumor maintenance. Thus, abrogation of Myc function in this class of tumors should have therapeutic benefit without significant side effects of normal tissues that are not dependent on high levels of Myc for survival. Indeed, Soucek et al have demonstrated that systemic inhibition of c-Myc in adult mice bearing K-RASG12D-induced lung tumors efficiently caused regression of these tumors whereas side effects were well tolerated over an extended period of time (up-to 28 days of continuous inhibition). All effects on normal tissues were rapidly and completely reversible (no discernable pathology within 1 year after treatment). Thus, in some embodiments, the cancer treated by the disclosed methods and compositions includes breast cancer, colon cancer, prostate cancer, cervical cancer, ovarian cancer, Burkitt's lymphoma, and/or melanoma.

IV. Method of Use

In an aspect the disclosure provides a method of treating cancer comprising administering to a patient in need thereof a therapeutically effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In an aspect the disclosure provides a method of treating cancer comprising administering to a patient in need thereof a therapeutically effective amount of a compound having a structure (I)

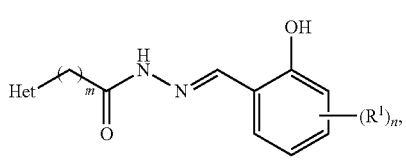

where $R^1$ is alkyl, OH, amino, alkoxy, aryl, alkenyl, alkynyl, or alkylenearyl, Het is heteroaryl, and m and n are each independently 0, 1, 2, 3, or 4. In an embodiment, Het is acridinonyl, diazolyl, triazolyl, or tetrazolyl. In an embodiment, Het is substituted with one or more of aryl, alkyl, amino, alkylenecycloheteroalkyl, heteroaryl, and alkyleneamino. In an embodiment, Het is substituted with one or more of $CH_3$, $CH_2CH_3$, $NH_2$, $N(alkyl)_2$, phenyl, oxadiazolyl, $CH_2$amino, $CH_2$tetrahydroisoquinolinyl, and $CH_2$azocanyl. In an embodiment, $R^1$ is $N(alkyl)_2$ or $CH_3$. In various embodiments, m can be 0, 1, 2, 3, or 4. In various embodiments, n can be 0, 1, 2, 3, or 4.

In an aspect the disclosure provides a method of treating cancer comprising administering to a patient in need thereof a therapeutically effective amount of a compound selected from the group consisting of N77A7, Compound 1, Compound 2, Compound 3, Compound 4, Compound 5, Compound 6, and Compound 7.

In various embodiments the cancer is selected from the group consisting of nueroblastoma, alveolar rhabomyosarcoma, retinoblastoma, small cell lung cancer, melanoma, breast cancer, colon cancer, prostate cancer, ovarian cancer, cervical cancer, lymphoma, and leukemia.

In an embodiment, the compounds of the method of treating cancer inhibit the function of a Myc protein selected from the group consisting of N-Myc, c-Myc, and L-Myc.

In an embodiment, the compounds of the method of treating cancer further comprise administering a therapeutically effective amount of an anti-cancer agent.

In an aspect the disclosure provides a method of treating an autoimmune disease comprising administering to a patient in need thereof a therapeutically effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In an aspect the disclosure provides a method of treating an autoimmune disease comprising administering to a patient in need thereof a therapeutically effective amount of a compound having a structure (I)

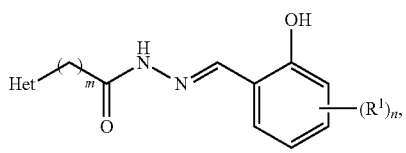

where $R^1$ is alkyl, OH, amino, alkoxy, aryl, alkenyl, alkynyl, or alkylenearyl, Het is heteroaryl, and m and n are each independently 0, 1, 2, 3, or 4. In an embodiment, Het is acridinonyl, diazolyl, triazolyl, or tetrazolyl. In an embodiment, Het is substituted with one or more of aryl, alkyl, amino, alkylenecycloheteroalkyl, heteroaryl, and alkyleneamino. In an embodiment, Het is substituted with one or more of $CH_3$, $CH_2CH_3$, $NH_2$, $N(alkyl)_2$, phenyl, oxadiazolyl, $CH_2$amino, $CH_2$tetrahydroisoquinolinyl, and $CH_2$azocanyl. In an embodiment, $R^1$ is $N(alkyl)_2$ or $CH_3$. In various embodiments, m can be 0, 1, 2, 3, or 4. In various embodiments, n can be 0, 1, 2, 3, or 4.

In an aspect, the disclosure provides a method of treating an autoimmune disease comprising a compound selected from the group consisting of N77A7, Compound 1, Compound 2, Compound 3, Compound 4, Compound 5, Compound 6, and Compound 7. In various embodiments, the autoimmune disease is selected from the group consisting of Goodpasture's syndrome, Crohn's Disease, Graves' Disease, Lupus erythematosus, Multiple Sclerosis, Psoriasis, Rheumatoid arthritis, and Relapsing polychondritis.

In an aspect, the disclosure provides a method of treating an autoimmune disease comprising a compound that inhibits the function of a Myc protein selected from the group consisting of N-Myc, c-Myc, and L-Myc.

In an aspect, the disclosure provides a method of inhibiting cell proliferation comprising contacting a cell with an effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In an aspect, the disclosure provides a method of inhibiting cell proliferation comprising contacting a cell with an effective amount of a compound having a structure (I)

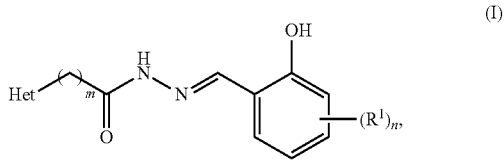

where $R^1$ is alkyl, OH, amino, alkoxy, aryl, alkenyl, alkynyl, or alkylenearyl, Het is heteroaryl, and m and n are each independently 0, 1, 2, 3, or 4. In an embodiment, Het is acridinonyl, diazolyl, triazolyl, or tetrazolyl. In an embodiment, Het is substituted with one or more of aryl, alkyl, amino, alkylenecycloheteroalkyl, heteroaryl, and alkyleneamino. In an embodiment, Het is substituted with one or more of $CH_3$, $CH_2CH_3$, $NH_2$, $N(alkyl)_2$, phenyl, oxadiazolyl, $CH_2$amino, $CH_2$tetrahydroisoquinolinyl, and $CH_2$azocanyl. In an embodiment, $R^1$ is $N(alkyl)_2$ or $CH_3$. In various embodiments, m can be 0, 1, 2, 3, or 4. In various embodiments, n can be 0, 1, 2, 3, or 4.

In an aspect, the disclosure provides a method of inhibiting cell proliferation comprising contacting a cell with an effective amount of a compound selected from the group consisting of N77A7, Compound 1, Compound 2, Compound 3, Compound 4, Compound 5, Compound 6, and Compound 7.

In an embodiment, the cell is a tumor cell.

In an aspect, the disclosure provides a method of inhibiting tumor cell growth comprising contacting a tumor cell with an effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In an aspect, the disclosure provides a method of inhibiting tumor cell growth comprising contacting a tumor cell with an effective amount of a compound having a structure (I)

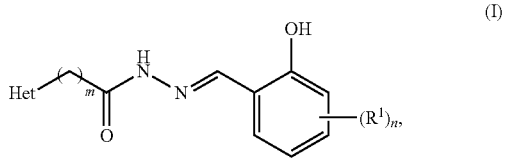

where $R^1$ is alkyl, OH, amino, alkoxy, aryl, alkenyl, alkynyl, or alkylenearyl, Het is heteroaryl, and m and n are each independently 0, 1, 2, 3, or 4. In an embodiment, Het is acridinonyl, diazolyl, triazolyl, or tetrazolyl. In an embodiment, Het is substituted with one or more of aryl, alkyl, amino, alkylenecycloheteroalkyl, heteroaryl, and alkyleneamino. In an embodiment, Het is substituted with one or more of $CH_3$, $CH_2CH_3$, $NH_2$, $N(alkyl)_2$, phenyl, oxadiazolyl, $CH_2$amino, $CH_2$tetrahydroisoquinolinyl, and $CH_2$azocanyl. In an embodiment, $R^1$ is $N(alkyl)_2$ or $CH_3$. In various embodiments, m can be 0, 1, 2, 3, or 4. In various embodiments, n can be 0, 1, 2, 3, or 4.

In an aspect, the disclosure provides a method of inhibiting tumor cell growth comprising contacting a tumor cell with an effective amount of a compound selected from the group consisting of N77A7, Compound 1, Compound 2, Compound 3, Compound 4, Compound 5, Compound 6, and Compound 7.

In an aspect, the disclosure provides a method of treating an infection comprising administering to a patient in need thereof a therapeutically effective amount of a compound selected from the group consisting of N423F7, N60C8, N49C4, N171H10, N117E2, N18C5, N117G10, N269D8, N144G3, N103A8, N121F3, N6A8, N4D2, N147A7, N47E10, N147G5, N77A7, N4G6, Compound 1, Compound 2, Compound 3, Compound 4, Compound 5, Compound 6, and Compound 7.

In an aspect, the disclosure provides a method of treating an infection comprising administering to a patient in need thereof a therapeutically effective amount of a compound having a structure (I)

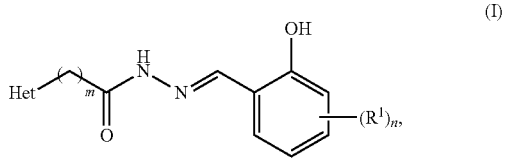

where $R^1$ is alkyl, OH, amino, alkoxy, aryl, alkenyl, alkynyl, or alkylenearyl, Het is heteroaryl, and m and n are each independently 0, 1, 2, 3, or 4. In an embodiment, Het is acridinonyl, diazolyl, triazolyl, or tetrazolyl. In an embodiment, Het is substituted with one or more of aryl, alkyl, amino, alkylenecycloheteroalkyl, heteroaryl, and alkyleneamino. In an embodiment, Het is substituted with one or more of $CH_3$, $CH_2CH_3$, $NH_2$, $N(alkyl)_2$, phenyl, oxadiazolyl, $CH_2$amino, $CH_2$tetrahydroisoquinolinyl, and $CH_2$azocanyl.

In an embodiment, $R^1$ is $N(alkyl)_2$ or $CH_3$.

In various embodiments, m can be 0, 1, 2, 3, or 4.

In various embodiments, n can be 0, 1, 2, 3, or 4.

In an aspect, the disclosure provides a method of treating an infection comprising administering to a patient in need thereof a therapeutically effective amount of a compound selected from the group consisting of N77A7, Compound 1, Compound 2, Compound 3, Compound 4, Compound 5, Compound 6, and Compound 7.

EXAMPLES

The following examples are provided for illustration and are not in any way to limit the scope of the disclosure.

Example 1

MYC Readout System

N-myc amplified neuroblastoma cells contain many copies of the N-myc gene and thus high levels of N-myc protein. In addition, many N-myc amplified cell lines are only semi-adherent and prone to clumping during manipulations. Therefore, such cells are not suitable for cell-based chemical screening. In contrast, SH-EP neuroblastoma cells, which express low level c-myc and no N-myc, are adherent, can be manipulated as a single cell suspension, and can readily express N-myc upon introduction of an N-myc expressing construct, which can be blocked with N-myc-specific shRNA (FIG. 1A). Therefore, SH-EP cells represented an ideal system for the creation of a cell-based readout system for screening small molecule chemical libraries for anti-myc compounds. To this end, SH-EP cells were stably transfected with a luciferase reporter gene under the control of a minimal heat shock protein promoter that contained 6 copies of the E-box sequence needed for N-myc specific transactivation and selected with G418, resulting in the identification of clone SHR6-17, the readout cell line.

Figure 2:
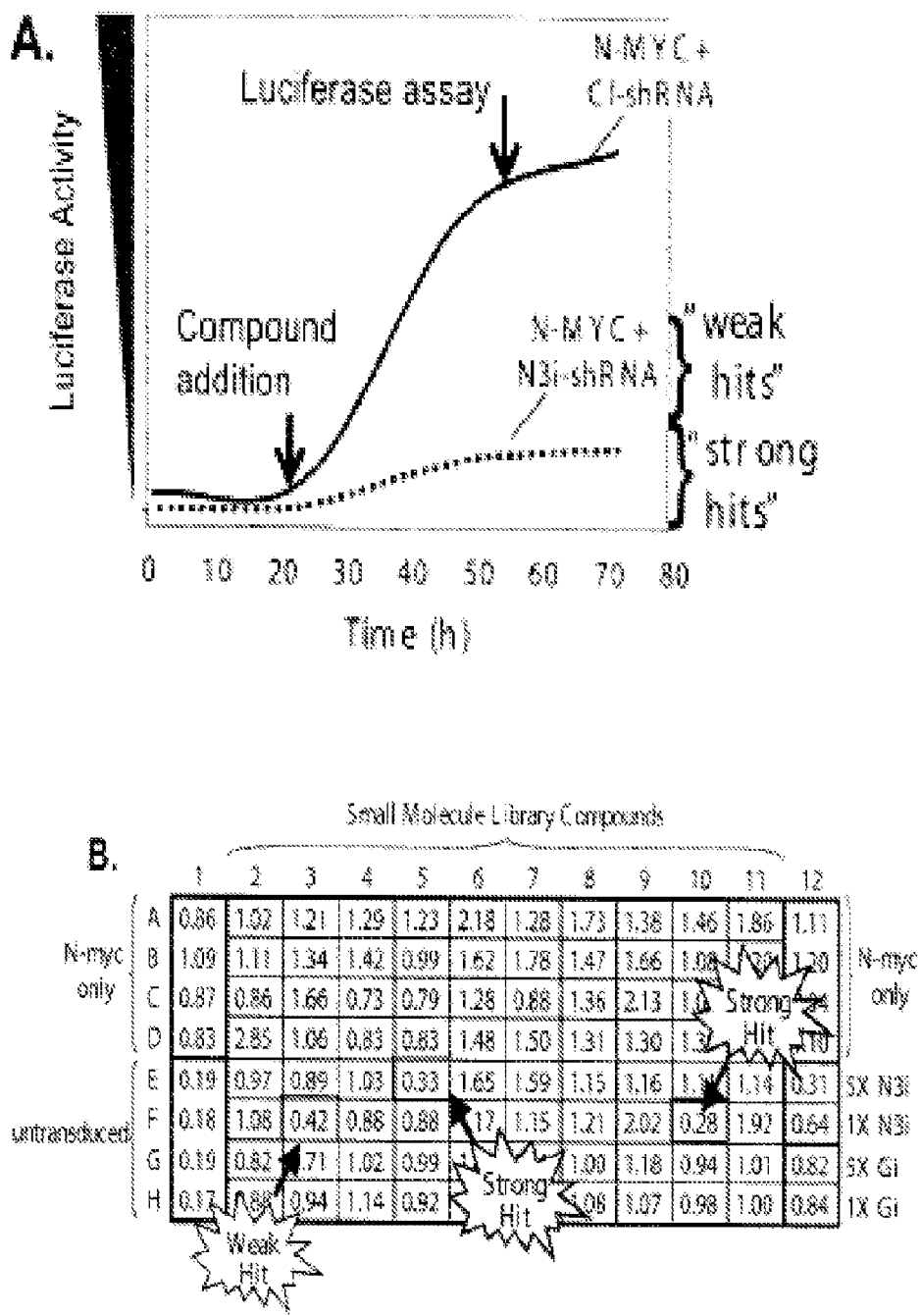
FIG. 2 depicts a schematic representation of the primary screen for MYC compounds. SHR6-17 cells with low basal levels of luciferase reporter activity were transduced with N-myc lentivirus. 24 h post-transduction, library compounds were added and luciferase activity of cells was measured ~24 h after incubation with compounds. N3i, an N-myc shRNA lentivirus, served as a positive control for inhibition of N-myc driven reporter activity. Two categories of hits were obtained: strong hits returned luciferase activity back to baseline or to siRNA levels and weak hits reduced luciferase activity ~40-60%. (B) Representative plate from primary screening of a 34,000 DIVERSet ChemBridge small molecule library. 80 library compounds were tested per 96 well plate and the level of luciferase activity in the presence of compound was compared to that of the average of the luciferase activity in cells transduced with N-myc (N-myc only) to produce an inhibition ratio as presented in the table. Strong hits represent those compounds that reduce the luciferase activity back to basal levels or to a level equivalent to that obtained with the highest N-myc siRNA (N3i) dose. Weak hits reduce the luciferase levels to 40-60% of the control. Gi are wells transduced with an siRNA control virus. Two strong hits and one weak hit were identified on this plate.

A schematic of the N-myc inhibitor readout system is presented in FIG. 1B. Transduction with N-myc lentivirus results in a 5-10 fold induction of luciferase reporter activity by 48 h compared to untransduced cells. For the screen, SHR6-17 cells (in 96 well plates) were transduced with N-myc lentivirus. Controls present in each screen were untransduced cells (basal reporter activity), N-myc siRNA (positive control) and control siRNA. Library compounds (80 per plate, 34,000 compounds total) were added to cells ~24 h after transduction to ensure that hits could repress N-myc function prior to expression of large levels of N-myc that might prevent the identification of weaker hits but did not interfere with viral transduction. After 24 h, a period sufficient for the degradation of luciferase (half-life ~3 h) in N-myc inhibited cells, luciferase activity was measured. In order to identify hits, an inhibition ratio was calculated (ratio between the luciferase activity of test compounds to that of the N-myc only control). To find a balance between identifying predominantly luciferase inhibitors and missing potentially important weak hits, we established two categories of hits: strong hits (inhibition ratio between ratios for untransduced and N3i transduced cells) and weak hits (inhibition ratio 0.4-0.6 or 40-60% N-myc only controls). During the primary screening, we identified 107 strong hits and 161 weak hits, which corresponded to a hit rate of ~0.79% that was well within our predicted hit rate of 1% based on previous experience with other cell-based readout systems. An example of the screening results for one plate is presented in FIG. 2.

Example 2

Filtering of Hits

Figure 3:
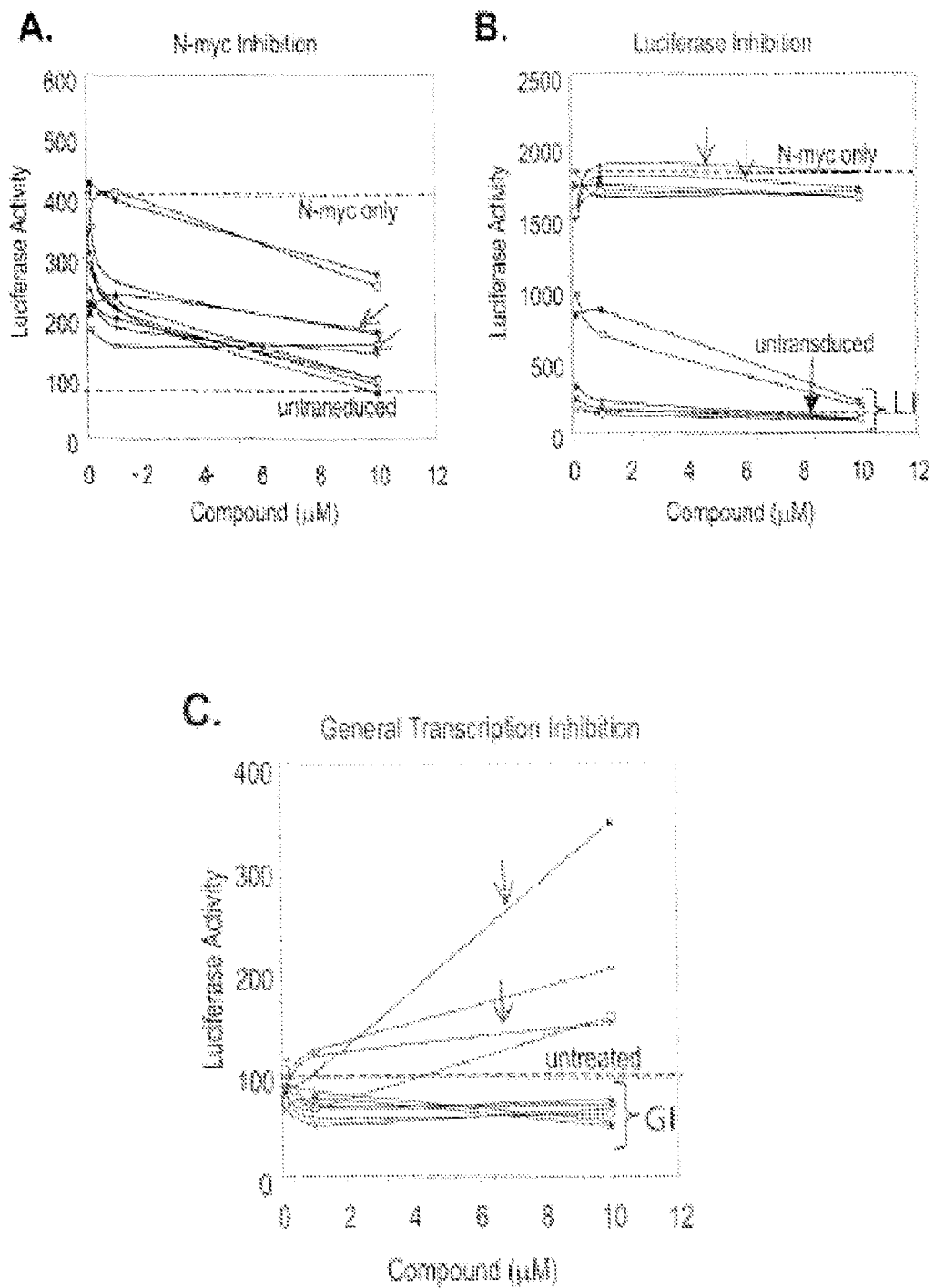
FIG. 3 illustrates filtering assays for validation of primary hits. (A) Primary hits were retested at three concentrations in the SHR6-17 N-myc lentiviral readout system. (B) Filtering of hits for luciferase inhibitors/quenchers. SHR6-17 cells were exposed to putative N-myc inhibitors 48 h after N-myc lentiviral transduction and then assayed for luciferase activity. Luciferase inhibitors (LI) return luciferase activity levels back to the level of untransduced cells. (C) Filtering for general transcriptional inhibitors. HCT116-NF-kB-luc reporter cells containing a non-N-myc responsive reporter were incubated with putative N-myc inhibitors for 24 h and then assayed for luciferase activity. General transcriptional inhibitors (GI) reduce reporter activity below basal levels. Validated hits (arrows in A, B, C) are active in the N-myc inhibition assay but not in the two filtering assays.

To eliminate false positives, a series of filters were applied to the "hits" identified in during primary screening. These filters included general toxicity, direct luciferase inhibitors/ quenchers and proteosome inhibitors/general transcription inhibitors. All these categories of compounds can cause a reduction in measurable luciferase activity in the absence of specificity to the intended target (i.e., N-myc). Prior to assaying for luciferase activity, each test well was subjected to microscopic evaluation to eliminate toxic compounds (total of 2353 toxic compounds in library). Once compounds were designated hits, they were re-screened at three different doses (~0.1, 1 and 10 µM) to verify activity (e.g., FIG. 3A). In parallel, the "hits" were assayed for direct luciferase inhibition using a short incubation (30 min) of SHR6-17 cells with a putative hit 48 h after transduction (i.e., maximum induction) (e.g., FIG. 3B) and general transcriptional/proteasome inhibition using a non-specific luciferase reporter (e.g., FIG. 3C). Filtering resulted in 68 validated hits (28 strong hits (26.2%) and 40 weak hits (24.8%).

Example 3

Secondary Filter; Myc-Specificity

Figure 4:
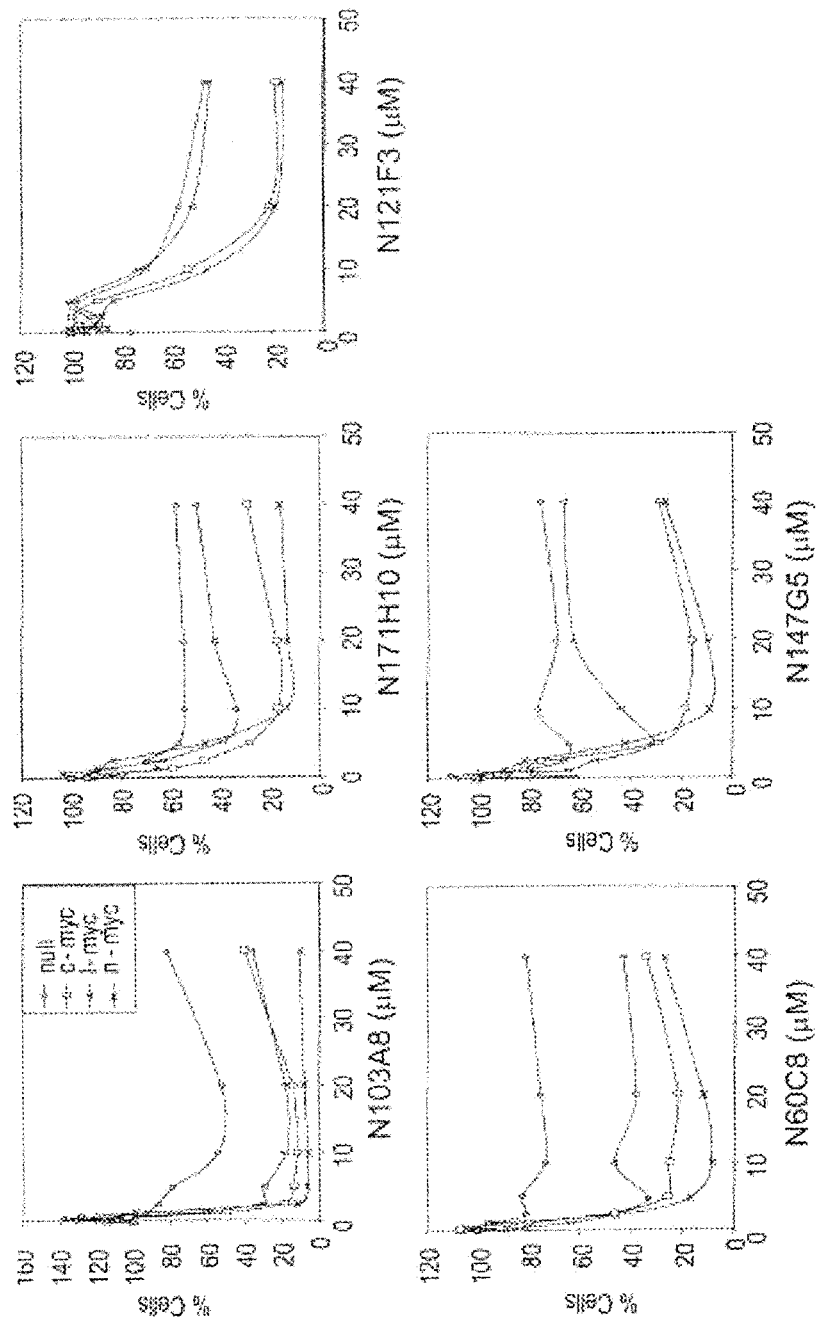
FIG. 4 illustrates the myc specificity of tested compounds. Rat1a cells expressing c-myc, L-myc or N-myc or lacking any Myc (null) were treated for 72 h with a range of hit compound concentrations. The cells were then fixed and stained with methylene blue and the percentage of cells in the presence of compound compared to DMSO only control was calculated. Data for 5 hits demonstrating greater activity in cells expressing Myc family members is presented.

Validated hits were divided into classes when two or more compounds shared significant structural similarity. The ID50 for N-myc transactivation (the inhibitory dose resulting in 50% decrease in luciferase activity) for each hit was calculated from the dose-response N-myc responsive reporter assay. Compounds within each class were ranked by their ID50 for N-myc transactivation and the best compounds within each class were chosen for further studies. In addition, the best of the structurally unique compounds were also analyzed. A total of 46 hits were passed through a secondary filter designed to determine the specificity of the hits for Myc proteins. For this filter, we used a panel of cell lines derived from Rat1a cells (kindly provided by Michael Cole, Dartmouth University): HO-null-c-Myc deficient cells due to homologous recombination that express neither N-myc nor L-myc HO-c-Myc, HO-L-myc and HO-N-myc derived by retroviral transduction of the corresponding Myc genes into HO-null cells. Since each cell line expresses only a single Myc or no Myc family members, we could identify compounds that act through Myc family members as well as which Myc family members. In the filtering assay, each of the cell lines was treated with a range of compound concentrations for 72 h and then stained with methylene blue, which was later eluted and measured to generate growth curves and to calculate ID50s for cell growth inhibition in each of the cell lines. Although many of the hits tested did not show a preference for Myc expressing cells compared to null cells, we clearly had a panel of hits that preferentially targeted Myc expressing cells (18 hits (8 strong hits and 10 weak hits); e.g., FIG. 4). In fact, several hits exhibited greater efficacy against particular Myc proteins suggesting the possibility of identifying both molecules that can distinguish between Myc family members in addition to pan-Myc inhibitors. The 18 Myc-specific compounds identified during the screening and filtering process are presented in Table 1 and represent distinct classes of molecules, including pyrazoles (e.g., N147A7, N47E10, N147G5), tetrazoles (e.g., N77A7) and 3-bromophenol (e.g., N4G6).

Figure 5:
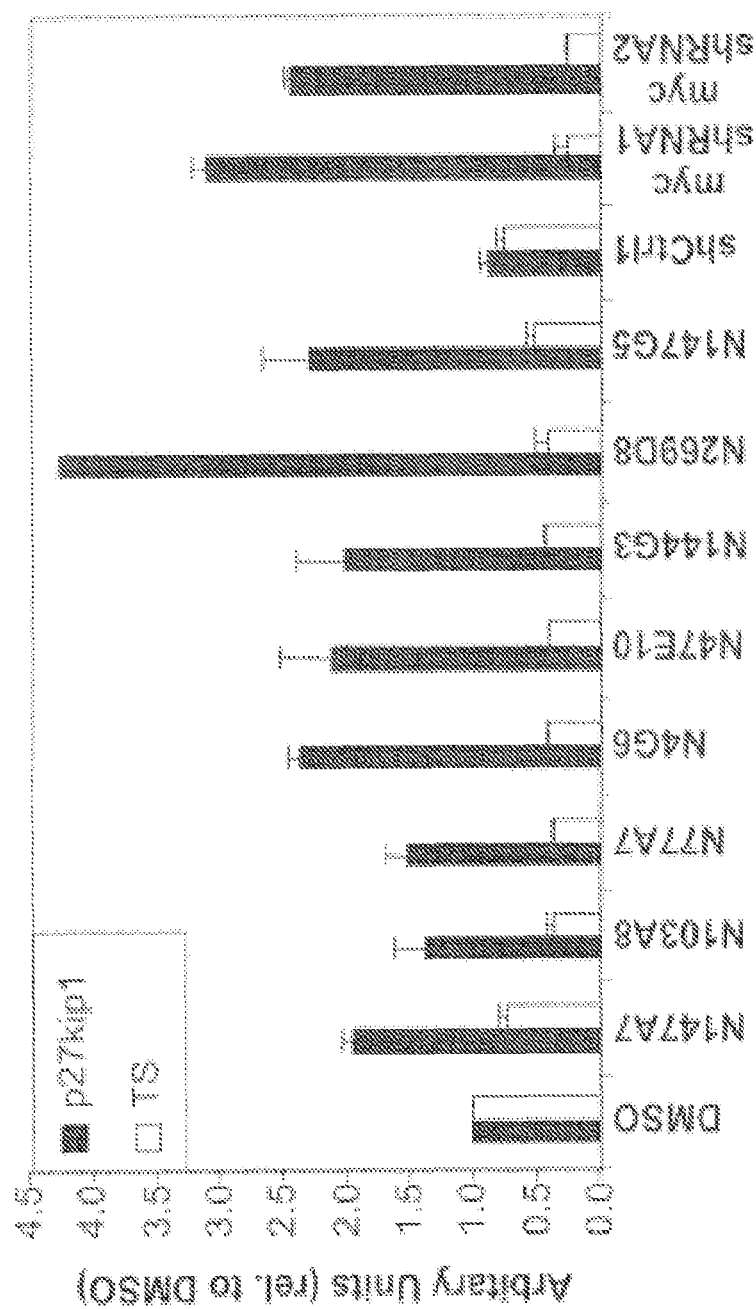
FIG. 5 illustrates the effect of putative Myc inhibitors on myc target expression levels in tumor cells. Real time per data for the expression of two myc targets (p27kip1 and thymidylate synthase (TS)) in melanoma cells following treatment with Myc inhibitors. Data is presented relative to DMSO vehicle control. Myc shRNA was used as a positive control.

To further verify that the Myc inhibitors were indeed directed at our desired target (i.e., Myc or a a component of a Myc related pathway(s)), we evaluated the effect of a series of hits on myc target genes using thymidylate synthase as an example of a transactivated gene and p27kip1 as an example of a repressed gene. When melanoma cells, which overexpress c-Myc, were treated with our compounds, the compounds caused a marked increase in the transcription of the Myc repressed gene and at the same time repression of the Myc activated gene similar to the effect of myc shRNA (FIG. 5). Thus, this subset of hits appears to be targeting Myc.

Example 4

Effect of Myc Inhibitors Against Tumor Cells

Figure 6:
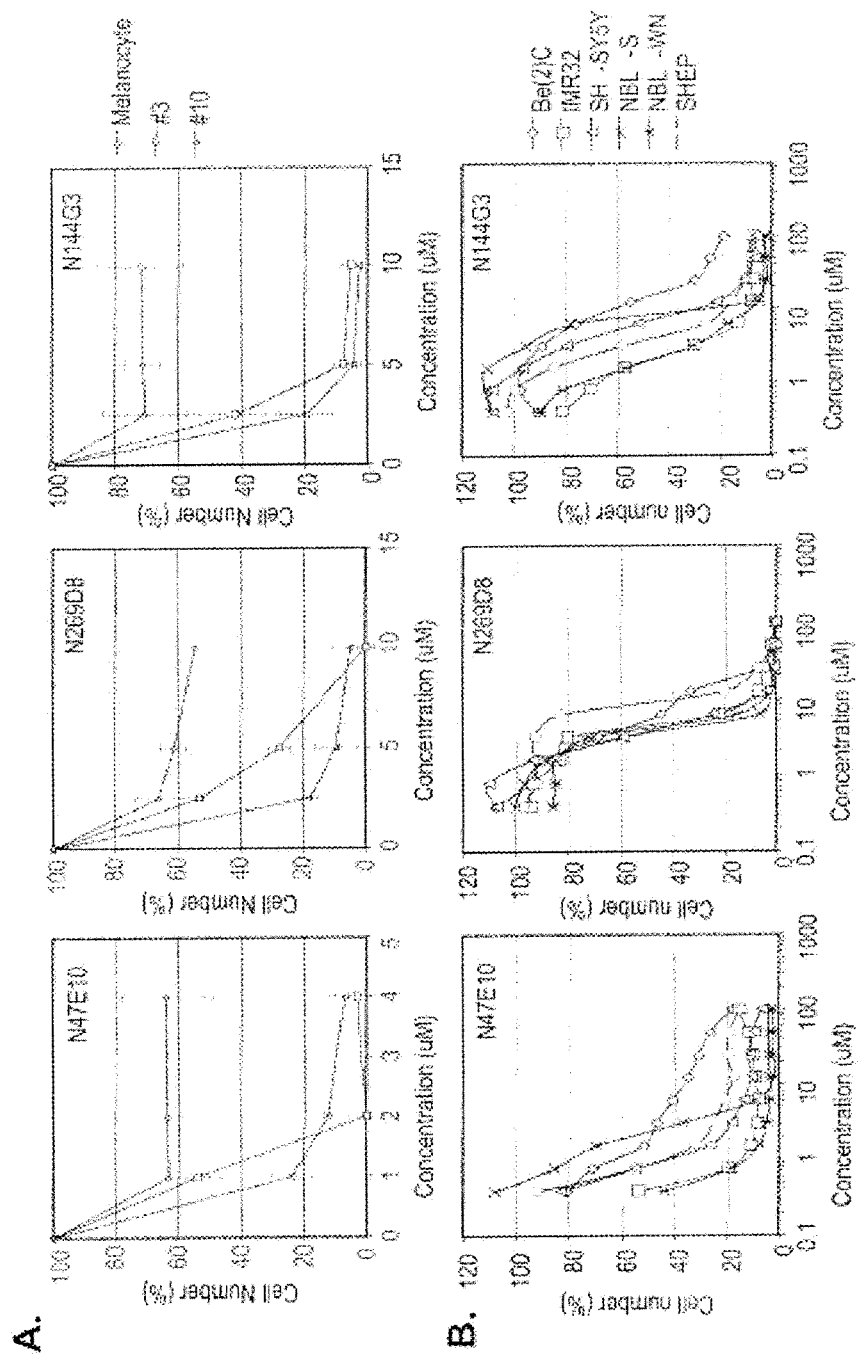
FIG. 6 illustrates putative Myc inhibitors that are efficacious against tumor but not normal cells. Melanocytes and melanoma (#3 and #10) (A) and neuroblastoma (B) were incubated in the continuous presence of Myc inhibitors for 72 h and cell growth/viability determined by standard MTS and resazurin methods, respectively. Data for three hits is presented as a percent of DMSO vehicle control.
Figure 7:
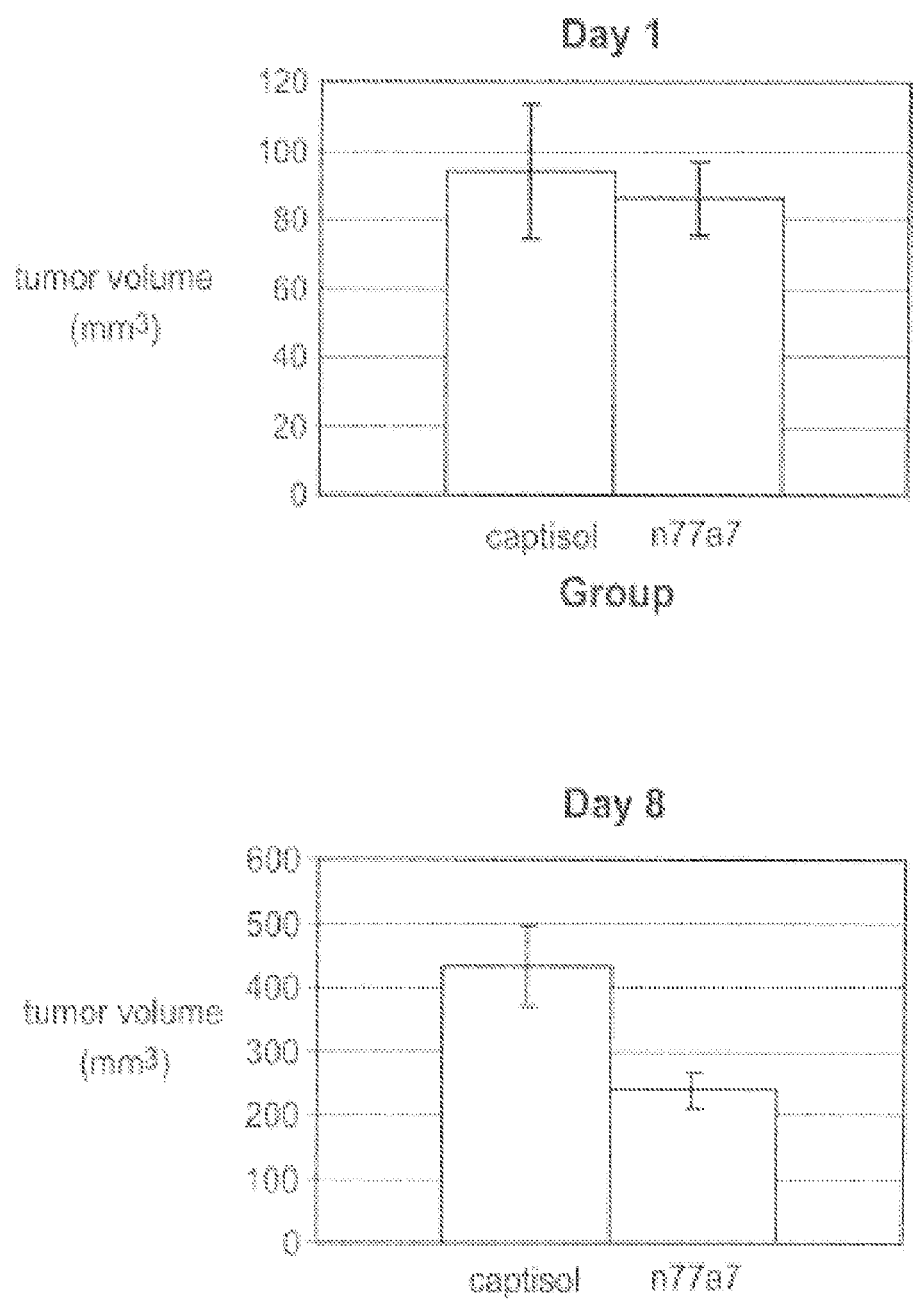
FIG. 7 depicts the results after athymic nude mice were inoculated with $1 \times 10^6$ SK-Mel-103 melanoma cells at 2 sites. One week following inoculation, treatment with 50 mg/kg N77A7 or Captisol vehicle control commenced. Treatment occurred daily by ip administration. Tumors were measured biweekly. Tumor volume was calculated using the formula tumor volume=$L \times W^2/2$, where W=shortest dimension.

Our Myc inhibitors were tested for their effect against a panel of tumor cell lines, including neuroblastoma and melanoma that represent cell lines with aberrant N-myc and c-Myc expression, respectively. This panel of cell lines included the human neuroblastoma lines BE(2)C, IMR32 and NBL-WN (N-myc amplified), NBL-S (N-myc overexpression), SH-SY5Y (significant N- and c-Myc expression) and SH-EP (low levels c-Myc only) as well as two melanoma cell lines (#3 and #10-c-Myc overexpression) and normal melanocytes). We found that our selected hits effectively inhibited/killed all of the cell lines tested with the exception of the normal melanocytes (e.g., FIG. 6). Interestingly, some hits were more toxic to the N-myc amplified cell lines, IMR32 and NBL-WN than to SH-EP cells, which do not have aberrant Myc expression (e.g., N269D8), suggesting that tumor cells that depend on abnormal Myc levels for survival may be selectively targeted by the inhibitors. The lack of toxicity in melanocytes is encouraging and may indicate that our molecules may inhibit tumors without causing significant general toxicity. Indeed, preliminary testing in vivo against a melanoma xenograft with one Myc inhibitor (N77A7) at ½ its maximum tolerated dose resulted in reduced tumor growth compared to the vehicle control in the absence of any observable toxicity (FIG. 7).

Example 5

Advantages and Improvements Over Existing Methods

Figure 8:
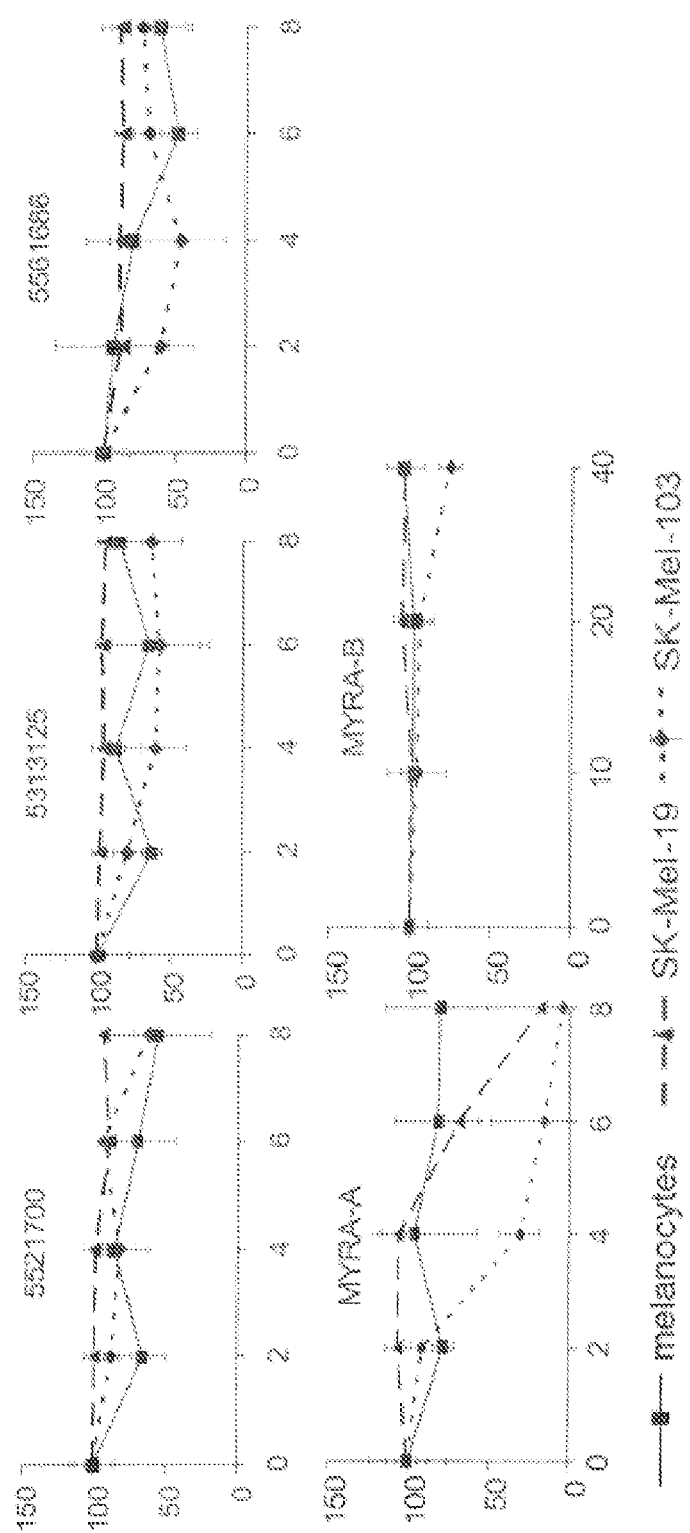
FIG. 8 depicts the testing of previously reported MYC-Max inhibitors against melanoma. SK-Mel-19, SK-Mel-103 cells and normal melanocytes with the above compounds at different concentrations for 72 h. Upon completion of the assay, cells were fixed and stained with methylene blue and the dye was eluted. Data is the % cells relative to the vehicle control.

Several groups have identified small molecule inhibitors that interfere with c-Myc-max dimerization using in vitro systems centered around the binding of the bHLH domains of c-Myc and max (Berg et al., 2002; Yin et al., 2003). Firstly, Berg et al (Berg et al., 2002) identified antagonists of c-Myc/max dimerization by fluorescently labeling the bHLH domain of each dimer partner and then screening for compounds based on fluorescence resonance energy transfer (FRET). Two isolated compounds inhibited c-Myc-induced focus formation in chicken embryo fibroblasts and were later shown to specifically interfere with Myc/Max dimerization without affecting the dimerization of other transcription factors (Kiessling et al., 2006). Secondly, Prochownik and colleagues (Yin et al., 2003) identified several hits using a yeast two-hybrid screen that specifically inhibited c-Myc expressing Rat-1a cells compared to a matched c-Myc null cell line. However, these in vitro systems are limited because they are directed at a single protein-protein interaction and are performed outside of the normal context of the proteins, i.e., they do not take into account the additional protein interactions that occur in vivo. A cell-based readout system has an advantage over traditional in vitro screening systems in that the selection of candidate molecules is performed under conditions that are closer to the final application for the compounds. Such a system is not limited to a single protein-protein interaction but has the possibility of identifying several classes of inhibitors working through different mechanisms of action (e.g., blocking Myc interactions with different proteins, inhibition of DNA binding, inhibition of nuclear localization). Indeed, testing of the previously reported Myc-max complex inhibitors in our system of melanoma demonstrated that these molecules were inactive or weak (FIG. 8) compared to our own molecules (e.g., FIG. 6).

Example 6

Identification of N77A7 as an Inhibitor of the N-myc Oncoprotein

Overview

N77A7 was identified in a small molecule library screen for inhibitors of the N-myc oncoprotein, which is involved in the pathogenesis of the childhood tumor neuroblastoma. The molecule is also effective against c-myc, a family member of N-myc that is overexpressed or amplified in a wide variety of tumors, including melanoma. In vitro, the effects of N77A7 on melanoma cells (e.g., SK-Mel-103) closely reflect the effects of myc shRNA on the same cells. In order to determine whether this in vitro effect can translate into an in vivo anti-tumor effect, we tested 50 mg/kg N77A7 administered daily ip against SK-Mel-103 xenografts established in athymic nude mice. Preliminary in vivo testing suggested that N77A7 may have had some anti-tumor effect (CBL2.5-01-Ms-1), however, some control tumors did not grow well and after a week of injection of the poorly soluble N77A7 (prepared in methylcellulose), there was severe peritonitis that may have contributed to poor absorption. Therefore, for this study, N77A7 was prepared in Captisol and injected in a larger volume so that N77A7 was completely soluble.

Methods

Animal study protocol CBL2.5-01-Ms-2. N77A7 formulated in Captisol was prepared. Both N77A7 and Captisol vehicle were prepared weekly according to the needs of the study. SK-Mel-103 melanoma cells ($1\times10^6$ cells/inoculation were inoculated into each rear flank of 20 athymic nude (7.5 week old males) on Sep. 11, 2009. Prior to commencement of treatment, mice were randomly assigned to treatment groups with 2 of 4 mice per cage assigned to the Captisol vehicle control group and the other 2 mice to the 50 mg/kg N77A7 group. When at least one tumor per mouse for the majority of mice reached ~50 mm$^3$ in tumor volume, treatment commenced. The first day of treatment (Day 1) was Sep. 21, 2009. Administration of N77A7 and vehicle control was performed daily by ip administration of 2.5 mg/ml solution of N77A7 or equivalent amount of vehicle control at 500 µl/25 g mouse body weight. Mouse body weight measurements were performed prior to commencement of treatment and Mondays-Wednesdays-Fridays thereafter. Administration volumes were adjusted during the course of the study based on the latest weight measurements. Treatments were administered. Tumor measurements were performed without prior knowledge of which treatment group each mouse belonged (i.e., blinded to treatment groups). When at least one tumor of a mouse reached 1000 mm$^3$ or tumor ulceration was evident, mice were euthanized according to the approved IACUC protocol (CBL 1096M). The experiment was completed on Day 18 (Oct. 8, 2009). At this time, 2 of the 4 remaining N77A7 treated mice had tumors that were ulcerated and 1 reached the tumor size endpoint without having any ulcerations. Since only one mouse remained in the study and would not be expected to affect the stats (one tumor getting close to the endpoint), the study was deemed over on Day 18.

Data analysis was performed. Analyses consisted of comparison of the mean tumor volume for each treatment group using unpaired t-test (p<0.05 is statistically significant). To control for variation in tumor sizes within each group at start of treatment, data was also analyzed as the mean fold tumor growth. To determine the fold tumor growth, the tumor volume for an individual tumor on Day X was divided by the tumor volume of the same tumor on Day 1 of the study. The mean fold tumor growth was compared between treatment groups using the unpaired t-test. In addition, the survival of mice in each treatment group was compared throughout the course of the study and statistically significant differences between the survival of the two treatment groups was determined using the logrank test. One last set analysis was to compare the time from start of treatment in which tumors reached 1000 mm3, the tumor volume endpoint set for this study based on the IACUC/animal welfare regulations that has established 2000 mm$^3$ as the total allowable tumor burden per mouse. Thus, since mice were inoculated in two locations, the total volume for each tumor cannot exceed 2000 mm$^3$. Therefore, using the assumption that both tumors will grow similarly within a mouse, the tumor size limit for a single tumor was set at 1000 mm$^3$ as approved in the IACUC protocol (CBL 1096M). Since both tumors were not at an identical size at start of treatment on a single mouse, only one tumor reached 1000 mm$^3$ at the time of euthanasia. Thus to determine the time to reach 1000 mm$^3$ for all tumors in each treatment group, the growth curve for each tumor was plotted and regression analysis was performed to obtain an equation for each curve. From the equation, the time to reach 1000 mm$^3$ tumor volume was calculated. The time to reach the tumor size endpoint for each treatment group was compared using the unpaired t-test.

Results

Mouse Survival.

Figure 9:
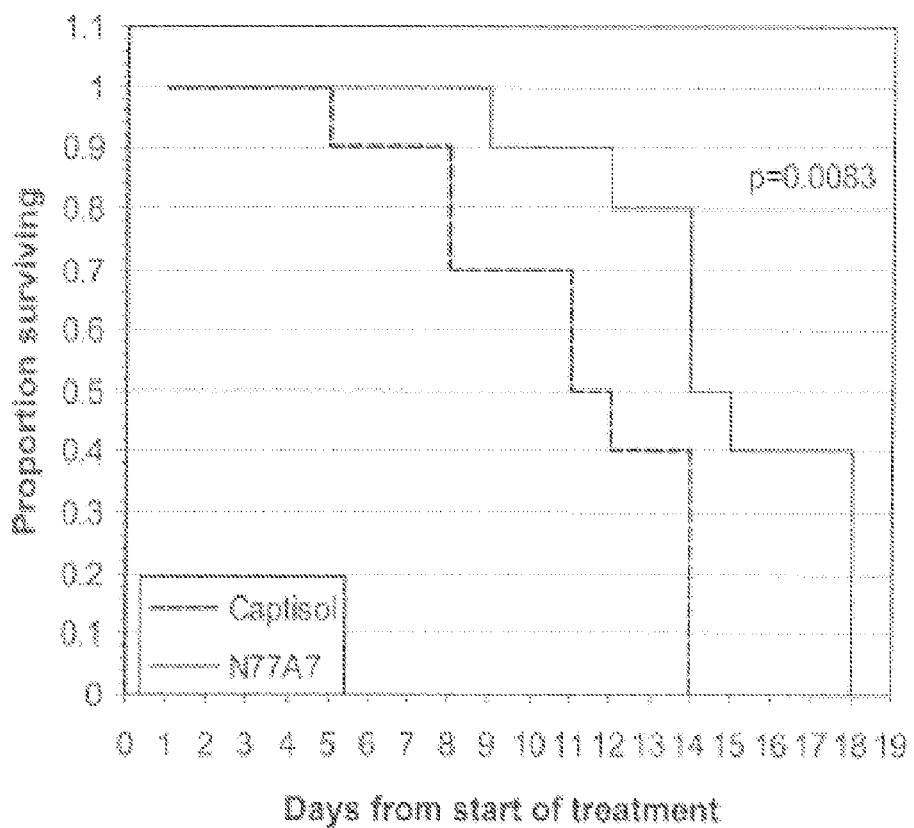
FIG. 9 illustrates the effect of N77A7 on survival of SK-Mel-103 tumor-bearing mice. Athymic nude mice were inoculated with $1 \times 10^6$ SK-Mel-103 tumor cells on each rear flank. When at least one tumor on the majority of mice reached ~50 mm$^3$, mice were randomly divided into treatment groups. Starting on Day 1 of treatment, mice were treated daily by ip injection of either 50 mg/kg N77A7 or the equivalent amount of Captisol vehicle. Mice were followed until tumors reached 1000 mm$^3$ or tumors ulcerated or 28 days of treatment, whichever came first. The proportion of surviving mice is depicted in the graph. The survival of N77A7 and vehicle control-treated mice was compared using the Log Rank test. p-value<0.05 indicates significance.

After 14 days of treatment, all Captisol-treated mice were euthanized due to reaching the tumor size limit of 1000 mm$^3$ or for tumor ulceration. In contrast, 5 of the 10 N77A7-treated mice remain in the study. A plot of proportion of surviving mice vs days of treatment is presented in FIG. 9. Comparison of the survival of the two treatment groups using the logrank test indicate a statistically significant difference (P=0.0083) in the effect of N77A7 and Captisol on mouse survival.

Mouse Weight and Condition.

Figure 10:
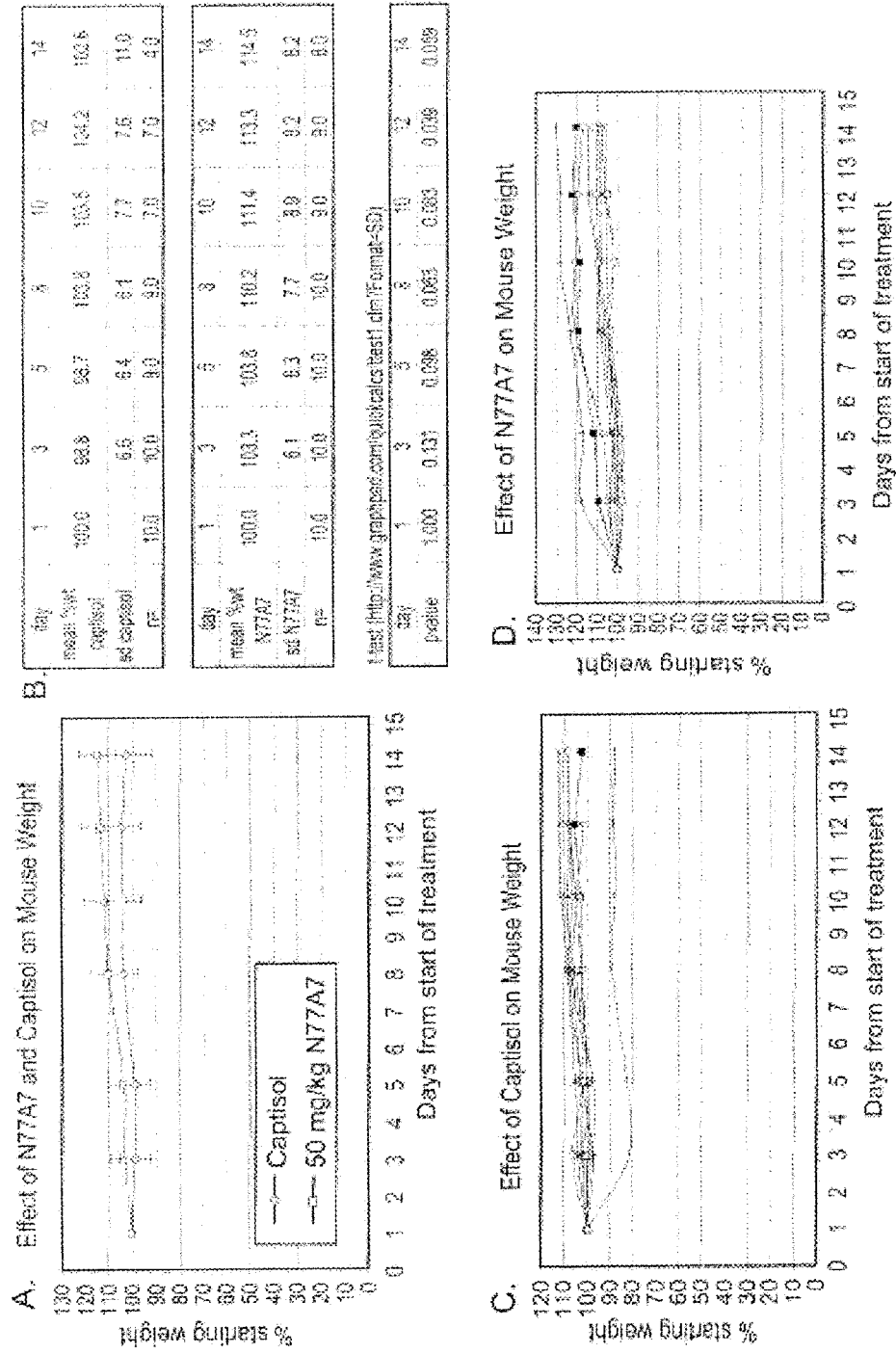
FIG. 10 illustrates the effect of Captisol and N77A7 on mouse weight. (A) Mean change in body weight as determined by calculating the % starting weight, which is the weight of a mouse on Day X divided by the weight of the same mouse on Day 1 and multiplied by 100. (B) Data values displayed graphically in (A), including mean % weight, standard deviation (sd), # of mice/group on a given day (n) and the p-values for the student t-test comparison of the two treatment groups on any given day. (C)-(D) Changes in mouse weight for individual mice in each treatment group calculated as described in (A).

In addition to comparing mouse survival, we analyzed the effects of the vehicle control and N77A7 on mouse weight. The data is presented in FIG. 10. N77A7 did not cause any weight loss after 14 consecutive days of treatment. In fact, several of the N77A7 mice appeared to gain some weight (FIG. 10D). In contrast, one of the 10 Captisol control mice lost a significant amount of its starting weight (FIG. 10C). However, this mouse regained 10% of the weight lost and never appeared sickly. There was no statistical differences between the weights of mice treated with Captisol compared to the N77A7 control, based on t-test analysis, with the exception of Day 12 where the p value=0.039 (FIG. 10B). No mice appeared sickly or in distress during the 16 days of the study so far. Tumors have been collected from a subset of mice for potential biochemical studies (e.g., senescence). Several N77A7 mice were also subjected to necropsy and there was no signs of compound precipitation within the abdominal cavity. More importantly, there were no signs of peritonitis that complicated the previous efficacy studies with this compound.

Effect on Tumor Growth.

Figure 11:
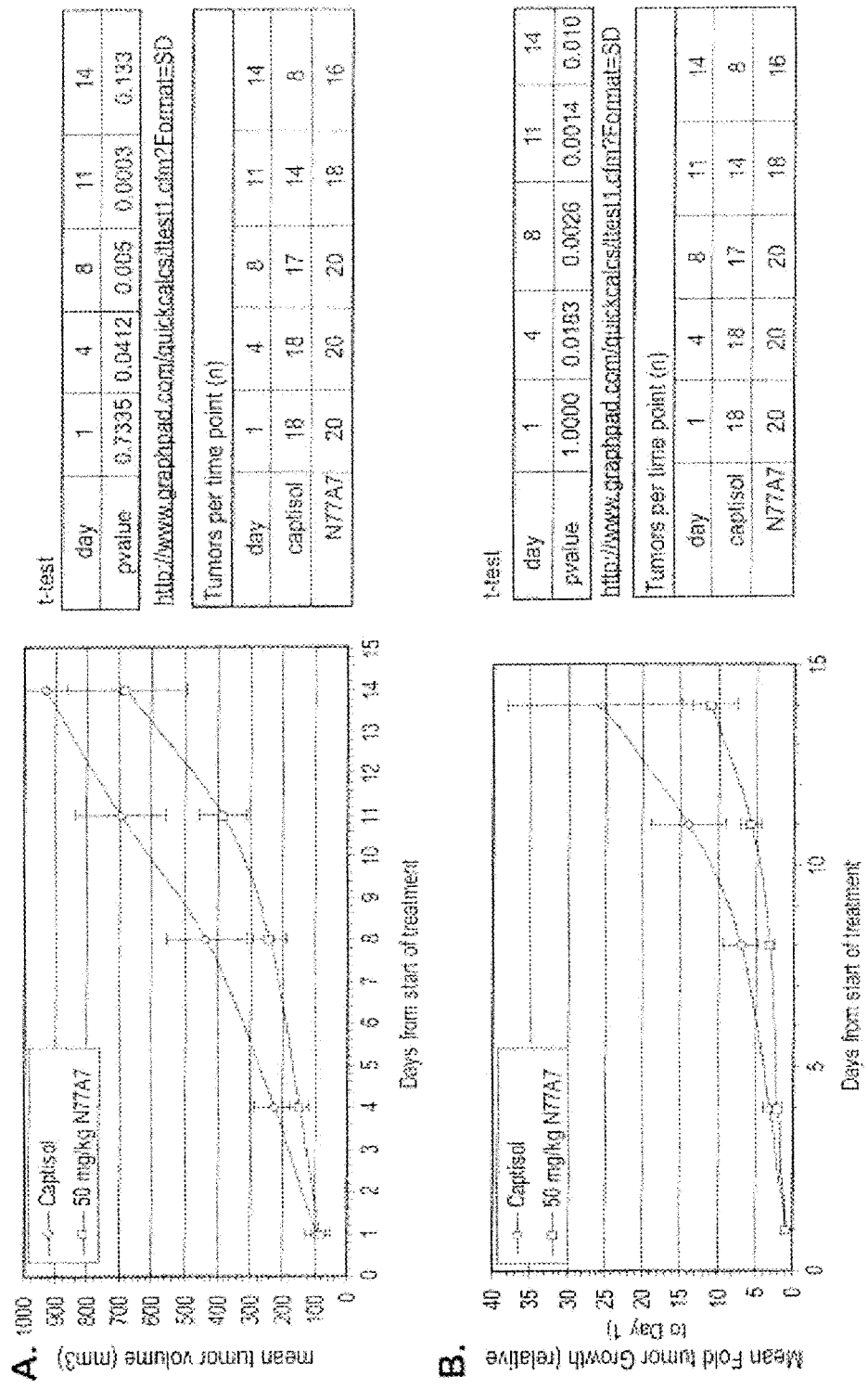
FIG. 11 illustrates the effect of 50 mg/kg N77A7 on tumor growth. (A) Athymic nude mice were inoculated with 1×106 SK-Mel-103 tumor cells in each rear flank. When at least one tumor on a mouse was ~50 mg for the majority of mice, treatment commenced. Mice were treated once daily ip with 50 mg/kg N77A7 or an equivalent amount of vehicle control (i.e., Captisol). Tumors were measured by digital caliper on Day 1 and then twice per week thereafter. Tumor measurements were made blind to the treatment each mouse received. Data is presented as the mean tumor volume on each measurement day. Comparison of tumor volume between treatment groups was made using unpaired t-tests. P value <0.05 is significant. (B) Same as (A) except data is presented as mean fold tumor growth, which was calculated by dividing the mean tumor volume on Day X by that of the same tumor on Day 1.

During the course of treatment, tumor measurements were made every 3-4 days using digital calipers and the tumor volume calculated using the following equation: $mm^3 = 1 \times w^2/2$ where 1 is the longest dimension and w is the shorter dimension measured perpendicular to the longest dimension. On each day of measurements, the mean tumor volume for N77A7 treated mice (n=18 tumors) were compared to that of the controls and statistical significance was determined using an unpaired t-test. In addition, to control for variations in sizes of tumors at the start of treatment, tumor volume on any given day was normalized to the tumor volume of the same tumor on Day 1 of treatment (i.e., fold tumor growth). These values were also compared between treatment groups using the unpaired t-test. The effects of N77A7 on tumor volume and fold tumor growth are illustrated in FIG. 11. A statistically significant, but rather small, difference between the tumors treated with N77A7 or Captisol was observed as early as on Day 4 (i.e., mice received 3 treatments prior to tumor measurement). A clear and discernable effect of N77A7 on tumor growth was observed on the remaining days of comparison with maximum tumor growth inhibition of ~45%. The differences between tumors from N77A7 and Captisol treated mice were statistically significant for days 4, 8 and 11 by both methods of analysis (FIG. 11). On day 14, the difference is not significant when mean tumor volume is compared but remains still statistically significant (p=0.01) when data is normalized to starting volume to correct for variability in starting tumor volumes. Note that while similar numbers of tumors were compared on Days 1-11, the number of tumors from Captisol treated mice drops by more than half on Day 14 due to euthanasia of the majority of Captisol treated mice because the tumor endpoint was reached. Therefore, on Day 14, the mean tumor volume data for Captisol group is skewed to a smaller size due to loss of the majority of large tumors reaching their endpoint. In addition, a subset of mice, developed more than one tumor on a given side of the mouse (left or right) despite a single inoculation (could be due to repositioning the needle or depth of needle for better placement of tumor). In these cases, the larger tumor of the two was chosen to follow by measurements. However, by Day 14, some of the tumors being followed in the study fused with the secondary tumor, thus lowering the accuracy of the final measurements. Therefore, the most reliable data for comparison purposes is up to Day 11. In follow-up studies, in cases of multiple tumors on one side, both tumors will be measured and the sum of the tumor volumes be analyzed such that when tumors fuse, there will be no ambiguity with the final measurements.

Figure 12:
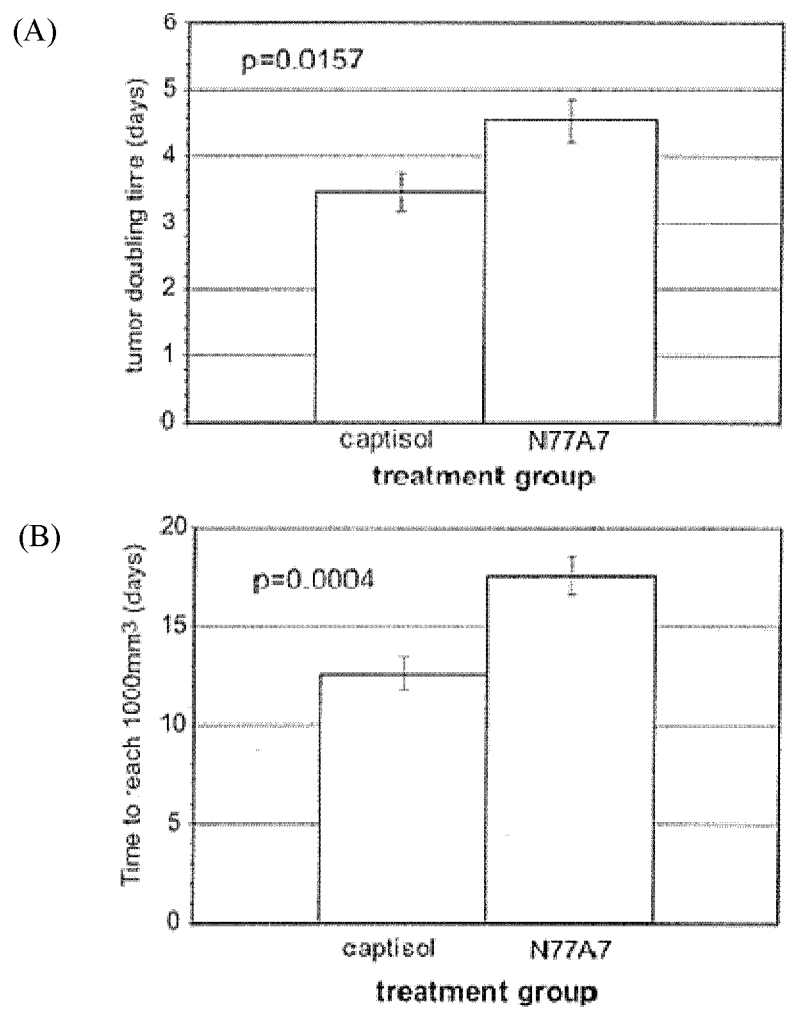
FIG. 12 illustrates the effect N77A7 on tumor doubling time and the time to reach 1000 mm$^3$ Growth curves for each tumor within each treatment group were plotted (tumor volume vs days from start of treatment). Regression analysis using the exponential trendline in Excel was used to generate an equation for each curve. From the equation, the tumor doubling time (A) and the time to reach the experimental endpoint of 1000 mm$^3$ was calculated. Error bars represent the standard error of the mean and p values were obtained using unpaired, two-sided t-tests.

Because both tumors on a mouse in most cases were not the same size at the start of treatment, only one tumor reached 1000 mm³ at time of euthanasia. In order to determine the time to reach 1000 mm³ for all tumors in each treatment group, growth curves were plotted for each tumor (tumor volume vs days from start of treatment) (FIG. 12). Regression analysis was performed on each curve (exponential trendline, Excel). From the equation of the curve, the doubling time and the time to reach the endpoint of 1000 mm³ was calculated. The mean doubling time and mean time to reach 1000 mm³ is presented in FIGS. 12A and 12B, respectively. Treatment with 50 mg/kg N77A7 increased the doubling time for tumor growth by 1 day (p=0.0157). In addition, the growth delay in reaching the study endpoint (i.e., 1000 mm3) was 5 days (p=0.0004).

Conclusions:

Based on the compilation of data from this study, N77A7 has a significant effect on tumor growth compared to vehicle control. This was supported by a statistically significant increase in survival, tumor doubling time and a 5 day delay in reaching the study endpoint as well as a maximum tumor growth inhibition of ~45%, which is considered a true anti-cancer effect (i.e., growth inhibition of ≥40% is considered a real effect by NCI standards). By Day 14, <50% starting tumors (8/18) were left in the study compared to 80% of the N77A7 treated mouse tumors, which can account for the drop off in significance and differences between the two groups since the control group was skewed towards smaller tumors due to removal of the majority of the large tumors (i.e., mice with large tumors being euthanized due to reaching tumor size endpoint or with tumor ulceration) prior to Day 14 measurements. In addition to the anticancer activity observed with N77A7, the use of Captisol as the vehicle and larger injection volume that enabled a lower concentration of drug to be administered appeared to overcome the issues with N77A7 precipitation and more importantly the peritonitis that was observed in previous efficacy testing. Therefore, it appears that N77A7 is now tolerable and the demonstration of in vivo efficacy indicates that further efforts around N77A7 are warranted.

Example 7

Use of Myc Inhibitors to Treat Infection

The compounds identified in the screen for inhibitors of the myc oncoprotein may also be used to treat infections. Infections which may be treated include bacterial infections, viral infections, fungal infections, and parasitic infections. For the prevention or treatment of infection, the appropriate dosage of compound will depend on the type of infection to be treated, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments.

The compositions will be formulated, dosed, and administered in a fashion consistent with good medical practice. Factors for consideration in this context include the particular infection being treated, the particular mammal being treated, the clinical condition of the individual patient, the causative agent of the infection, the site of delivery of the compound, the method of administration, the scheduling of administration, and other factors known to medical practitioners. The therapeutically effective amount of the compound to be administered will be governed by such considerations, and is the minimum amount necessary to prevent, ameliorate, or treat the infection. Such amount is preferably below the amount that is toxic to the host.

Example 8

N77A7 Affects C-MYC-Activated Global Gene Expression

SK-Mel-103 melanoma cells were infected with control- or MYC shRNA-expressing lentiviruses or treated with DMSO or 4 μM of N77A7. In 48 hours after lentiviral infection or incubation with the chemicals, cells were collected, RNA was isolated and subjected to global expression analysis using Affymetrix GeneChip® Human Genome U133 Plus 2.0

Figure 13:
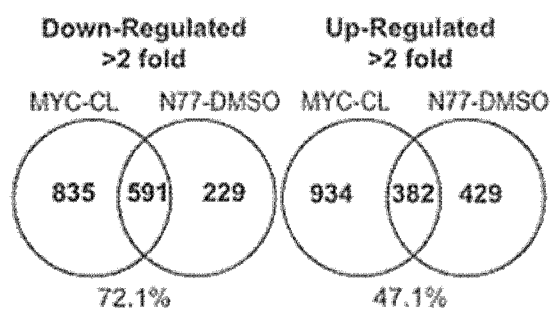
FIG. 13 illustrates a comparison of changes in global gene expression caused by depletion of C-MYC via shRNA or by treatment with N77A7.

Platform. A linear model specifically designed for microarray analysis was applied to the data. Differentially expressed probe sets were detected using a nested F-test approach. An adjusted p-value of 0.005 was used to assess significance, adjusting for multiple comparisons using false discovery rate. The obtained results are schematically represented in FIG. 13. It was determined that incubation with N77A7 negatively affected expression of 820 genes by ≥2 fold (591+229, FIG. 13). 591 of these genes (72.1%) were also suppressed ≥2 fold by MYC shRNA. Interestingly, only 47.1% of genes whose expression was induced by N77A7≥2 fold were also upregulated ≥2 fold by MYC shRNA. This difference (72.1% versus 47.1%) could be accounted for by the nature of our primary screening that was aimed at inhibition of C-MYC as a transcriptional activator and not as a transcriptional repressor. Therefore it is logical to expect that the number of genes whose expression is suppressed both by MYC-shRNA and N77A7 should be higher than the number of genes whose expression is induced by both treatments. These data further attest to the high specificity of N77A7 as an inhibitor of MYC-dependent transcriptional activation.

Example 9

Analogs of N77A7 with Improved In Vivo Efficacy 260 analogs of N77A7 were selected from several commercially available libraries of small molecules based on the structural similarities with N77A7. The compounds were screened for the ability to permanently suppress proliferation and induce senescence in cells from melanoma lines SK-Mel-19 and SK-Mel-103. Based on the above-described screening procedure, seven small molecules were identified as having IC50 values lower than that of N77A7. Table 3 illustrates the results of these experiments.

TABLE 3

| N77A7 Analogs with Improved IC50 Values | | |
|---|---|---|
| Compound | IC50 in SK-Mel-19 (µM) | IC50 in SK-Mel-103 (µM) |
| N77A7 | 3 | 3 |
| Compound 1 | 4 | 2.5 |
| Compound 2 | 0.4 | 0.4 |
| Compound 3 | 0.5 | 0.5 |
| Compound 4 | 0.15 | 0.1 |
| Compound 7 | 0.35 | 0.25 |
| Compound 6 | 0.35 | 0.25 |
| Compound 5 | 0.6 | 0.35 |

Additionally, several of the N77A7 analogs were subjected to the test for the metabolic stability in human and mouse liver microsomes. Briefly, 1 µM of test compound was incubated with microsomal protein (human liver microsomes: 0.5 mg/mL; mouse liver microsomes 0.5 mg/mL) and buffer (100 mM potassium phosphate, pH 7.4, 5 mM magnesium chloride). The positive control was 5 µM testosterone. The reaction was equilibrated at 37 C in a shaking water bath for 3 to 5 minutes. After equilibration, an aliquot was removed and combined with 50/50 acetonitrile/water containing 0.1% formic acid and internal standard to terminate the reaction. 1 mM NADPH was immediately added and the tube was returned to the water bath. Five sample time points were taken (0, 10, 20, 30, and 60 minutes). Aliquots were removed and combined with 50/50 acetonitrile/water containing 0.1% formic acid and internal standard to terminate the reaction. The samples were mixed for 10 minutes and centrifuged. The supernatant from each sample was diluted (if necessary) and then transferred to vials for analysis by LC-MS/MS for the test compound and internal standard without calibration standards. The percent remaining at each time point was determined by the test compound's peak area response ratio versus the 0 minute sample. The addition of the cofactor NADPH was confirmed at the conclusion of the study using fluorescence detection. As shown in Tables 4 and 5, metabolic stability of one N77A7 analog (5679402) was significantly higher than that of N77A7 (half-life of 13.5 minutes vs. 5.2 minutes in mouse liver microsomes and >60 minutes vs. 13.1 minutes in human liver microsomes).

TABLE 4

| Metabolic Stability in Mouse Liver Microsomes | | | | | | | |
|---|---|---|---|---|---|---|---|
| Test Compound | Percent Remaining | | | | | Half-life (min) | CL$_{int}$ (mL/min/mg protein) |
| | 0 min | 10 min | 20 min | 30 min | 60 min | | |
| N77A7 | 100 | 25 | 8.9 | 4.5 | <1.0 | 5.2 | 0.27 |
| Compound 2 | 100 | 45 | 32 | 26 | 21 | 13.5 | 0.10 |
| Compound 3 | 100 | 39 | 12 | 3.7 | <1.0 | 7.0 | 0.20 |
| Compound 4 | 100 | 3.1 | 1.8 | 1.3 | <1.0 | 2.0 | 0.69 |
| Compound 6 | 100 | 20 | 8.9 | 4.3 | 1.2 | 4.6 | 0.30 |
| Compound 7 | 100 | 26 | 7.1 | 3.8 | 1.4 | 5.2 | 0.27 |
| Testosterone | 100 | 19 | — | <1.0 | <1.0 | 4.2 | — |

TABLE 5

Metabolic Stability of N77A7 analogs in Human Liver Microsomes

| Test Compound | Percent Remaining | | | | | Half-life (min) | $CL_{int}$ (mL/min/mg protein) |
|---|---|---|---|---|---|---|---|
| | 0 min | 10 min | 20 min | 30 min | 60 min | | |
| N77A7 | 100 | 87 | 30 | 1– | <1.0 | 13.1 | 0.11 |
| Compound 2 | 100 | 119 | 91 | 83 | 74 | >60 | <0.02 |
| Compound 3 | 100 | 93 | 66 | 49 | 24 | 29.5 | 0.047 |
| Compound 4 | 100 | 56 | 37 | 28 | 20 | 16 | 0.087 |
| Compound 6 | 100 | 49 | 31 | 18 | 6.9 | 11.5 | 0.12 |
| Compound 7 | 100 | 46 | 25 | 20 | 11 | 10.7 | 0.13 |
| Testosterone | 100 | 78 | — | 40 | 19 | 23.9 | — |

Taken together, these results indicate that N77A7 and several of its analogs are effective inhibitors of MYC-dependent transcriptional activation. Thus, the compounds disclosed herein are useful to treat cancer by inhibiting the activity of the c-myc oncoprotein.

Example 10

TABLE 6

Ability to inhibit C-Myc-dependent proliferation in HO15.19 cells reconstituted with exogenous C-Myc

| Compound | (μM) | HO15.19-Vector | | | HO15.19-C-MYC | | |
|---|---|---|---|---|---|---|---|
| | | G0/G1 | G2 | S | G0/G1 | G2 | S |
| DMSO | | 50.76 | 22.12 | 27.12 | 35.43 | 34.05 | 30.51 |
| N77A7 | 3 | 54.9 | 23.88 | 21.22 | 49.73 | 15.39 | 34.88 |

In parallel, N77A7 was evaluated for the ability to inhibit C-MYC-dependent proliferation in HO15.19 cells reconstituted with exogenous C-MYC. HO15.19 cells are the only cell line that is capable of continuous proliferation in the absence of any MYC protein expression, a feature that makes this line a reference in the field. The cells were generated from immortalized rat fibroblasts (TGR) and exhibit slow growth rate due to significant accumulation of cells in the G0/G1 phase of the cell cycle (identifiable by fluorescence activated cell sorter analysis (FACS)). Reconstitution of these cells with C-MYC completely reverses the slow-growth phenotype accompanied with the reduced size of the G0/G1 peak in FACS analysis. As shown in Table 6, for N77A7, treatment of HO15.19-MYC cells significantly changed the percent of cells in G0/G1 stage of the cell cycle. At the same time, the percent of HO15.19-vector cells in G0/G1 phase of the cell cycle was not affected by N77A7 (Table 6).

Example 11

Figure 14A:
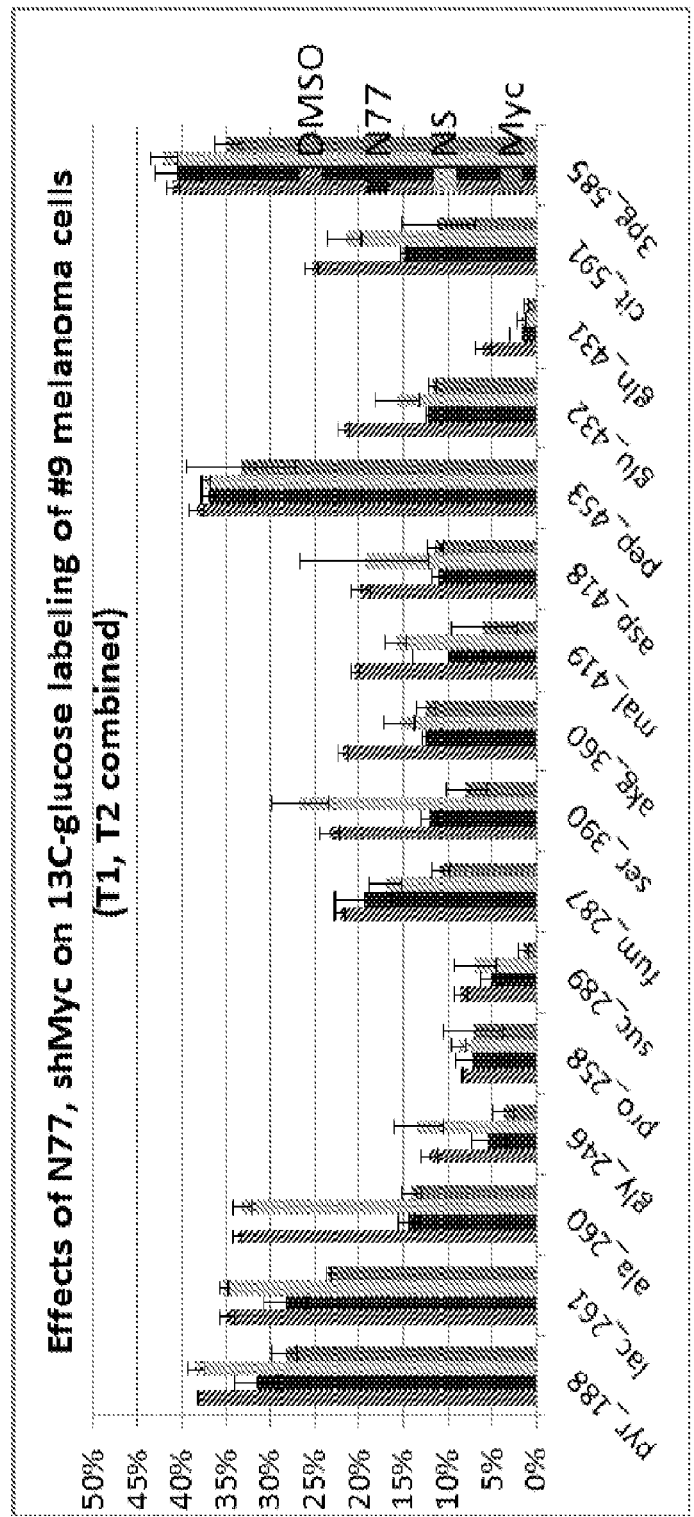
FIG. 14 shows an example of comparing some effects of genetic vs chemical suppression of MYC in on 13C-labeling of selected central metabolites in melanoma cells (Mel-9) grown in the presence of 13C-glucose (FIG. 14A) or 13C-glutamine (FIG. 14B). Cells were grown in 6-well plates, and the medium was replaced for the final 24 h of culture with the MEM medium described previously (Scott et al., JBC 286, 42626-34, 2011), containing 50% $^{13}$C-labeled [U-$^{13}$C$_6$] glucose or 50% $^{13}$C-labeled [U-$^{13}$C$_5$] glutamine] (Sigma-Aldrich). Metabolites were extracted and GC-MS analysis and calculation of $^{13}$C labeling were performed as described (Scott et al., 2011). Metabolites were quantified on the basis of fragment ion intensities and standard curves derived from mixtures of standards run concurrently with samples, using the program Metaquant (B. Bunk et al., Bioinformatics 22, 2962-2965, 2006). On the graphs, the 13C labeling percentage is shown as average of to separate experiments (with error bars). Samples from cells treated by antimycon ("N77"), anti-MYC shRNA ("Myc"), nonspecific shRNA ("NS") and the control treated only by DMSO are shown bars with distinct patterns. Note that labeling via glucose of serine, glycine, pyruvate, lactate, TCA-cycle metabolites was lower in N77A7-treated or MYC-shRNA-expressing cells compared to control counterparts.
Figure 14B:
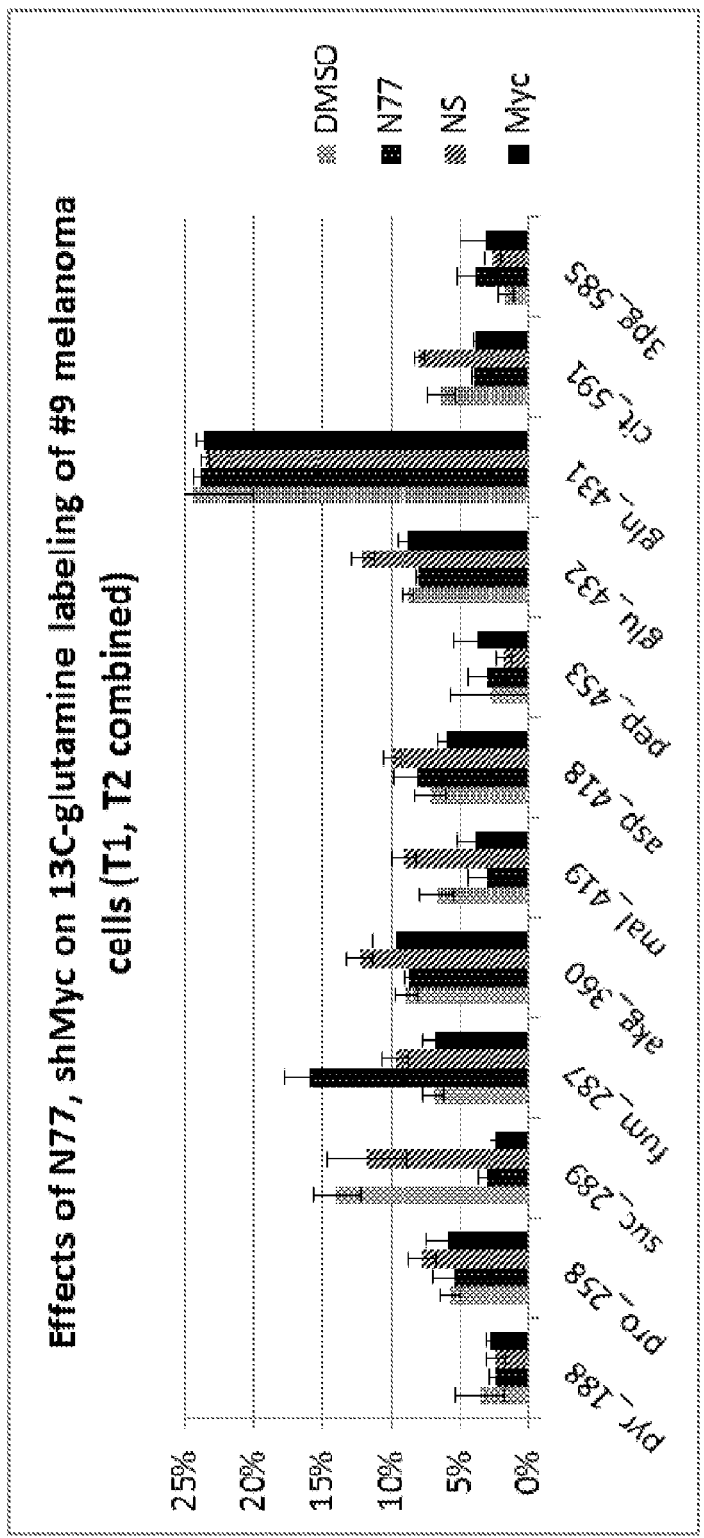

FIG. 14A-B: Labeling via glucose of serine, glycine, pyruvate, lactate, TCA-cycle metabolites was lower in N77A7-treated or MYC-shRNA-expressing cells compared to control counterparts.

Stable-isotope tracing was used to identify a set of changes of flux distribution in central metabolism caused by genetic inactivation of C-MYC (either via C-MYC shRNA in melanoma cells #9 (FIGS. 14A-B) or via knock-out of both alleles of C-MYC (HO15.19 myc-null cells, see above)) (FIGS. 15A-C) versus treatment with N77A7. As can be concluded form both set of Figures, suppression of C-MYC via genetic or pharmacological means demonstrated remarkable similarities with regard to changes in cell metabolism and are overall consistent with the known role of C-MYC as an enhancer of central metabolism including consumption of glucose.

Figure 15A:
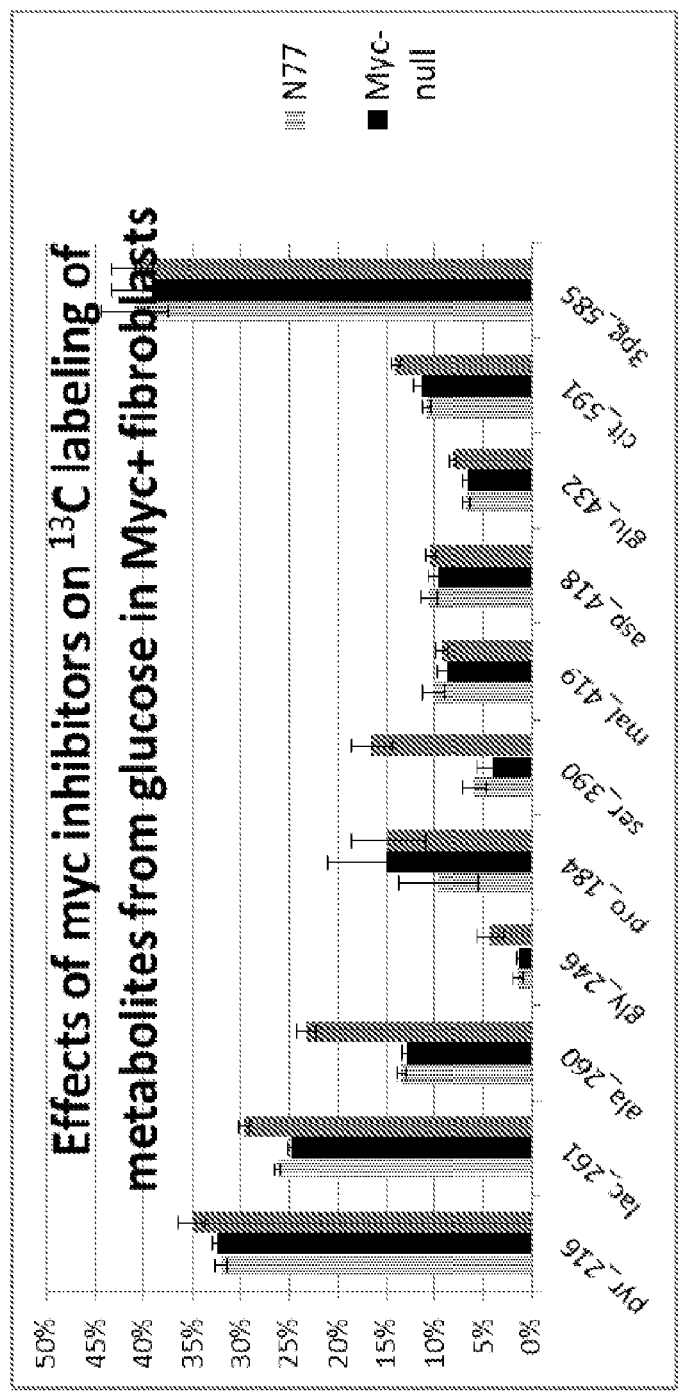
FIG. 15A shows an example of some effects of antimycon on $^{13}$C labeling of metabolites from glucose in Myc+ fibroblasts. $^{13}$C-labeling (%) for selected central carbon metabolites was determined by GC-MS after 24 hrs of biosynthetic labeling with $^{13}$C-glucose in HO15.19 Myc-null cells (solid bars) or in "Myc+"-cells (HO15.19 Myc-null cells with C-MYC re-expression), untreated (diagonal pattern) or treated (dotted pattern) with Antimycon. Experiments were perform and data were analyzed as described in FIG. 14. Cellular measurements are mean±SD of 3 samples. Note a comparable decrease in $^{13}$C-labeling (%) of Gly, Ser and Ala, as a result of either genetic or chemical MYC inactivation.
Figure 15B:
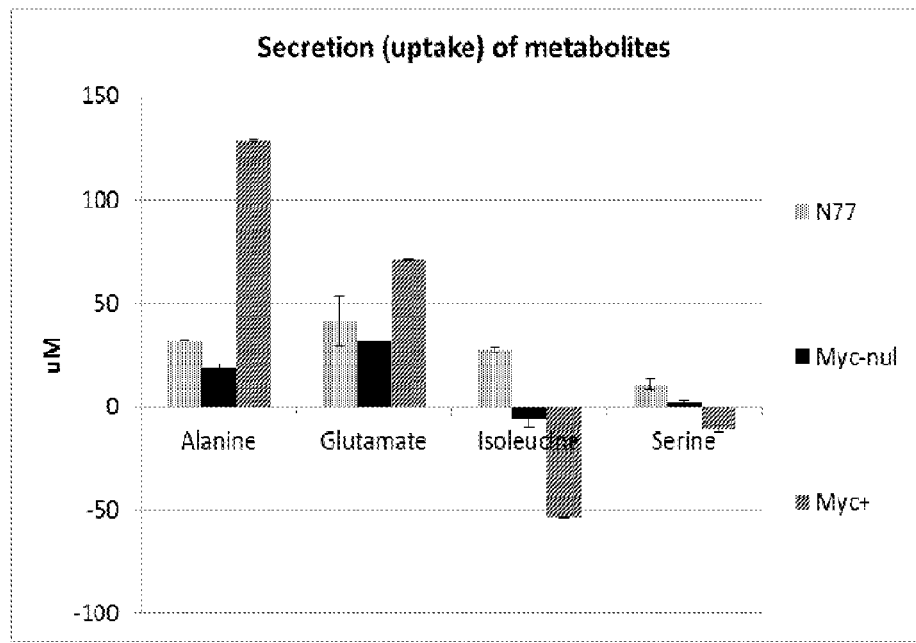
FIG. 15B shows an example of some effects of Antimycon on uptake/secretion of amino acids in Myc+ fibroblasts based on their detection in the conditioned media.
Figure 15C:
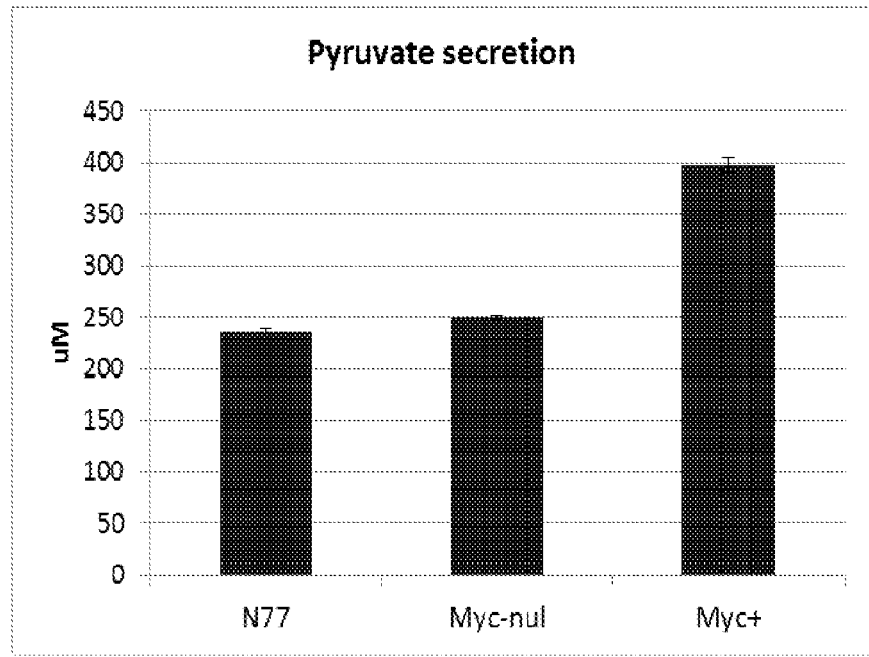
FIG. 15C shows an example of an effect of Antimycon on secretion of pyruvate in Myc+ fibroblasts. Note that Myc+ cells treated with Antimycon N77 generally have a metabolic phenotype similar to Myc-null cells.

FIG. 15A-C: Inhibitor N77 generally has a metabolic phenotype similar to Myc-null cells (but lower cellular fumarate).

What is claimed:

1. A method of inhibiting tumor cell growth comprising contacting a tumor cell with an effective amount of a compound having a structure (I)

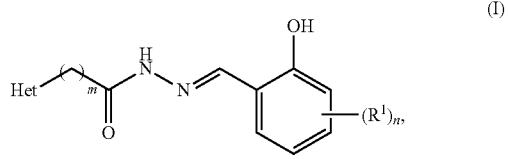

wherein $R^1$ is alkyl, OH, amino, alkoxy, aryl, alkenyl, alkynyl, or alkylenearyl, Het is heteroaryl, wherein one or more substituents on the heteroaryl group, if present, are independently selected from the group consisting of halo, alkyl, alkenyl, $OCF_3$, $NO_2$, CN, NC, OH, alkoxy, amino, $CO_2H$, $CO_2$alkyl, and heteroaryl, and m and n are each independently 0, 1, 2, 3, or 4.

2. The method of claim 1, wherein the compound is selected from the group consisting of

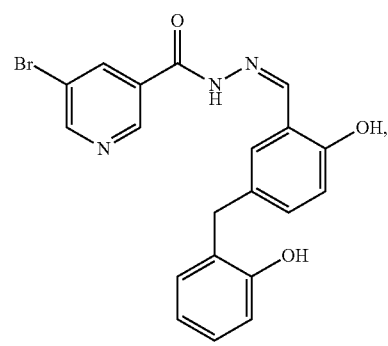

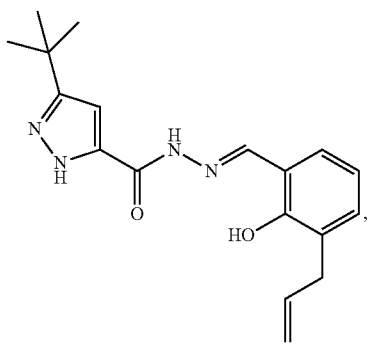
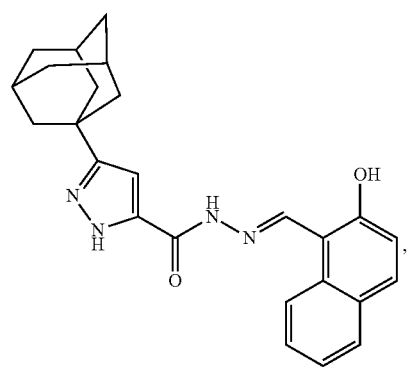
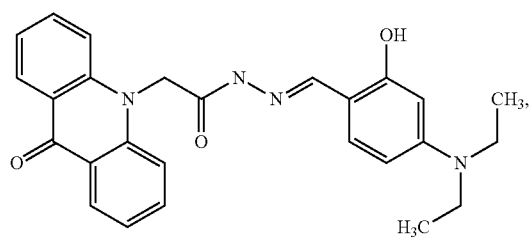
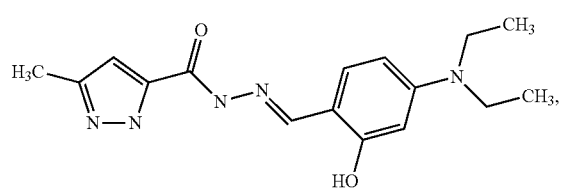
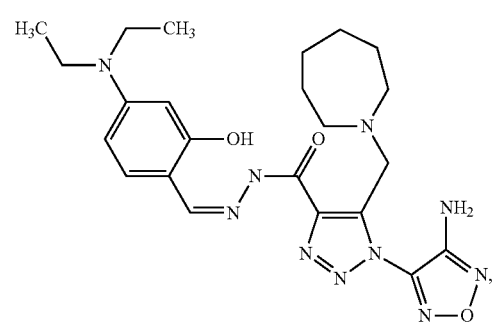

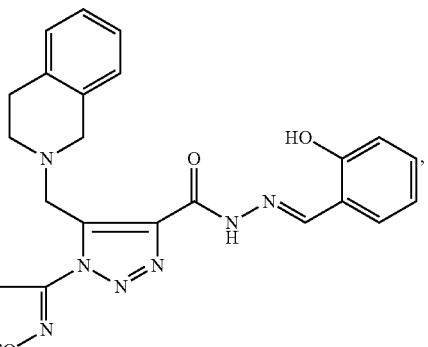
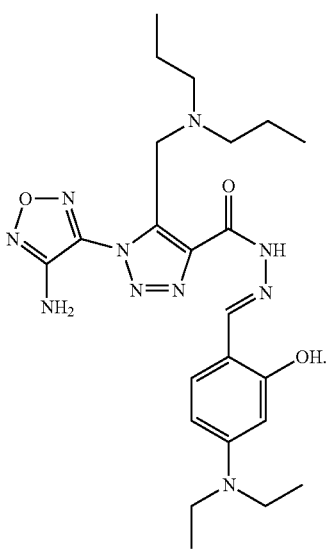

3. The method of claim 1, wherein Het is acridinonyl, diazolyl, triazolyl, or tetrazolyl.

4. The method of claim 1, wherein Het is substituted with one or more of alkyl, amino, alkylenecycloheteroalkyl, heteroaryl, and alkyleneamino.

5. The method of claim 1, wherein Het is substituted with one or more of $CH_3$, $CH_2CH_3$, $NH_2$, $N(alkyl)_2$, oxadiazolyl, $CH_2$amino, $CH_2$tetrahydroisoquinolinyl, and $CH_2$azocanyl.

6. The method of claim 1, wherein $R^1$ is $N(alkyl)_2$ or $CH_3$.

7. The method of claim 1, wherein m is 0 or 1.

8. The method of claim 1, wherein n is 0, 1, or 2.

9. The method of claim 1, wherein the compound is selected from the group consisting of 53
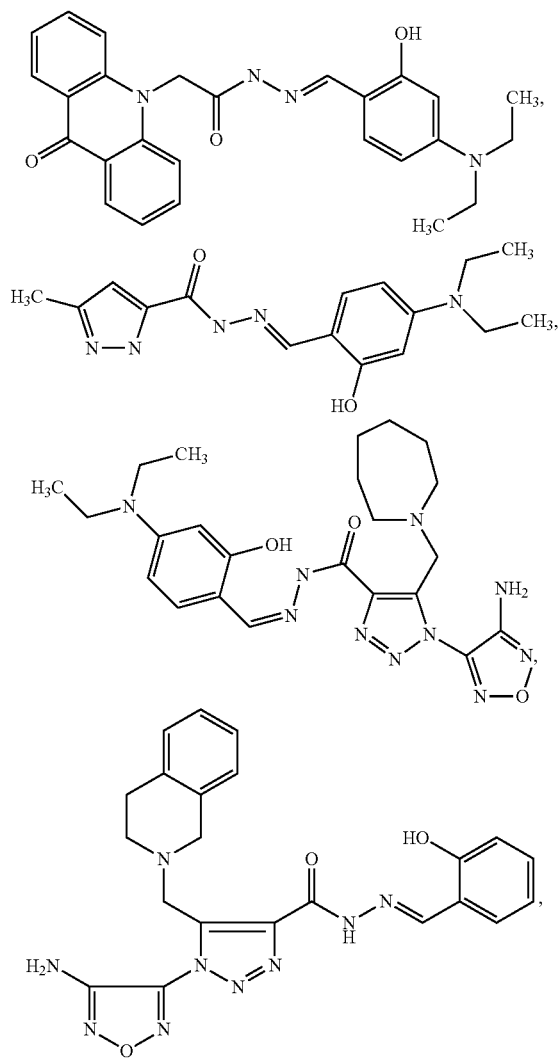
54
-continued
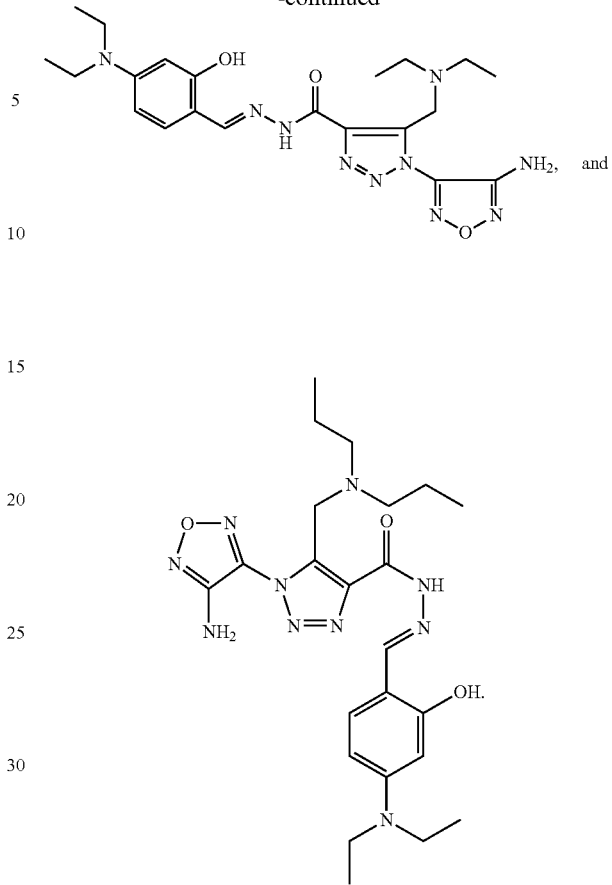
10. The method of claim 1, wherein the compound inhibits the function of a Myc protein selected from the group consisting of N-Myc, c-Myc, and L-Myc.
* * * * *